US008999383B2

(12) United States Patent
Lee et al.

(10) Patent No.: US 8,999,383 B2
(45) Date of Patent: Apr. 7, 2015

(54) COMPOSITIONS OF GNRH RELATED COMPOUNDS AND PROCESSES OF PREPARATION

(75) Inventors: Amanda Lee, Dublin (IE); Bozena Adamczyk, Dublin (IE); David C. Coughlan, Co Kildare (IE); Edel O'Toole, Dublin (IE); Thomas W. Leonard, Wilmington, NC (US)

(73) Assignee: Merrion Research III Limited (IE)

( * ) Notice: Subject to any disclaimer, the term of this patent is extended or adjusted under 35 U.S.C. 154(b) by 548 days.

(21) Appl. No.: 12/437,012

(22) Filed: May 7, 2009

(65) Prior Publication Data

US 2009/0280170 A1    Nov. 12, 2009

Related U.S. Application Data

(60) Provisional application No. 61/051,038, filed on May 7, 2008.

(51) Int. Cl.
| | | |
|---|---|---|
| *A61K 9/48* | (2006.01) | |
| *A61K 9/28* | (2006.01) | |
| *A61K 38/09* | (2006.01) | |
| *A61K 47/12* | (2006.01) | |
| *A61K 47/14* | (2006.01) | |

(52) U.S. Cl.
CPC ............ *A61K 9/2846* (2013.01); *A61K 9/4891* (2013.01); *A61K 38/09* (2013.01); *A61K 47/12* (2013.01); *A61K 47/14* (2013.01)

(58) Field of Classification Search
None
See application file for complete search history.

(56) References Cited

U.S. PATENT DOCUMENTS

| | | |
|---|---|---|
| 4,525,339 A | 6/1985 | Behl et al. |
| 4,590,062 A | 5/1986 | Jang |
| 4,654,155 A | 3/1987 | Kipp et al. |
| 4,656,161 A | 4/1987 | Herr |
| 4,764,375 A | 8/1988 | Paradissis |
| 4,786,508 A | 11/1988 | Ghebre-Sellassie et al. |
| 4,789,547 A | 12/1988 | Song et al. |
| 4,900,730 A | 2/1990 | Miyauchi |
| 4,996,058 A | 2/1991 | Sinnreich |
| 5,110,606 A | 5/1992 | Geyer et al. |
| 5,169,933 A | 12/1992 | Anderson et al. |
| 5,190,748 A | 3/1993 | Bachynsky et al. |
| 5,221,734 A | 6/1993 | Burk et al. |
| 5,229,130 A | 7/1993 | Sharma et al. |
| 5,288,497 A | 2/1994 | Stanley et al. |
| 5,346,701 A | 9/1994 | Heiber et al. |
| 5,444,041 A | 8/1995 | Owen et al. |
| 5,506,207 A | 4/1996 | Rivier et al. |
| 5,541,155 A | 7/1996 | Leone-Bay et al. |
| 5,631,347 A | 5/1997 | Baker et al. |
| 5,633,226 A | 5/1997 | Owen et al. |
| 5,639,469 A | 6/1997 | Benes et al. |
| 5,646,109 A | 7/1997 | Owen et al. |
| 5,650,386 A | 7/1997 | Leone-Bay et al. |
| 5,688,761 A | 11/1997 | Owen et al. |
| 5,707,648 A | 1/1998 | Yiv |
| 5,714,477 A | 2/1998 | Einarsson |
| 5,736,161 A | 4/1998 | Garces et al. |
| 5,807,983 A * | 9/1998 | Jiang et al. .................... 530/313 |
| 5,821,222 A | 10/1998 | Bonse et al. |
| 5,821,230 A | 10/1998 | Jiang et al. |
| 5,840,685 A | 11/1998 | Fujii et al. |
| 5,854,281 A | 12/1998 | Uekama et al. |
| 5,863,555 A | 1/1999 | Heiber et al. |
| 5,912,009 A | 6/1999 | Venkateshwaran et al. |
| 5,952,000 A | 9/1999 | Venkateshwaran et al. |
| 5,977,175 A | 11/1999 | Lin |
| 5,998,432 A | 12/1999 | Walsh et al. |
| 6,001,390 A | 12/1999 | Yum et al. |
| 6,004,984 A | 12/1999 | Goulet et al. |
| 6,015,801 A | 1/2000 | Daifotis et al. |

(Continued)

FOREIGN PATENT DOCUMENTS

| | | |
|---|---|---|
| CN | 1243667 A | 2/2000 |
| CN | 1606432 A | 4/2005 |

(Continued)

OTHER PUBLICATIONS

Hild, Sheri Ann et al: ("The ability of a gonadotropin-releasing hormone antagonist, acyline, to prevent irreversible infertility induced by the indenopyridine, CDB-4022, in adult male rats: the role of testosterone." Biology of Reproduction Jul. 2004, vol. 71, No. 1, Jul. 2004, pp. 348-358).*
PCT Search Report for International application No. PCT/US2009/002842.
Mishima et al., "Studies on the Promoting Effects of Medium Chain Fatty Acid Salts on the Nasal Absorption of Insulin in Rats," J. Pharmacobio-Dyn., 10:624-631 (1987).
Morishita et al, "Site-Dependent Effect of Aprotinin, Sodium Caprate, $Na_2EDTA$ and Sodium Glycocholate on Intestinal Absorption of Insulin," Biol. Pharm. Bull. 16:68-72 (1993).

(Continued)

*Primary Examiner* — Snigdha Maewall
(74) *Attorney, Agent, or Firm* — Myers Bigel Sibley & Sajovec, P.A.

(57) ABSTRACT

The present invention provides compositions of GnRH related compounds that are suitable for oral administration, injectable administration and other forms of administration wherein the gelling characteristics of the composition are a factor. The compositions of the present invention comprise a therapeutically effective amount of one or more GnRH related compound, and a sufficient amount of at least one anti-gelling agents to reduce the gelation of the GnRH related compound. The present invention also provides processes for preparation of a composition of one or more GnRH related compound, wherein the process comprises mixing the GnRH related compound with one or more anti-gelling agents, wherein the anti-gelling agent comprises a medium chain fatty acid salt, or an ester, an ether, or a derivative of a medium chain fatty acid and has a carbon chain length of from about 4 to about 20 carbon atoms or is a surface active agent.

32 Claims, 14 Drawing Sheets

(56) References Cited

U.S. PATENT DOCUMENTS

| | | |
|---|---|---|
| 6,017,559 A | 1/2000 | Mulqueen et al. |
| 6,017,944 A | 1/2000 | Chu et al. |
| 6,025,366 A | 2/2000 | Walsh et al. |
| 6,068,850 A | 5/2000 | Stevenson et al. |
| 6,077,847 A | 6/2000 | Walsh et al. |
| 6,077,858 A | 6/2000 | Goulet et al. |
| 6,124,261 A | 9/2000 | Stevenson et al. |
| 6,147,088 A | 11/2000 | Goulet et al. |
| 6,150,352 A | 11/2000 | Goulet et al. |
| 6,150,522 A | 11/2000 | Goulet et al. |
| 6,156,767 A | 12/2000 | Goulet et al. |
| 6,156,772 A | 12/2000 | Goulet et al. |
| 6,200,602 B1 | 3/2001 | Watts et al. |
| 6,214,798 B1 | 4/2001 | Semple et al. |
| 6,235,712 B1 | 5/2001 | Stevenson et al. |
| 6,248,363 B1 | 6/2001 | Patel et al. |
| 6,270,804 B1 | 8/2001 | Getz et al. |
| 6,296,881 B1 | 10/2001 | Hata et al. |
| 6,326,360 B1 | 12/2001 | Kanazawa et al. |
| 6,372,728 B1 | 4/2002 | Ungell |
| 6,379,960 B1 | 4/2002 | Popoff et al. |
| 6,468,559 B1 | 10/2002 | Chen et al. |
| 6,524,557 B1 | 2/2003 | Backstrom et al. |
| 6,638,530 B1 | 10/2003 | Ishibashi et al. |
| 6,747,014 B2 | 6/2004 | Teng et al. |
| 6,747,125 B1 | 6/2004 | Hoeger et al. |
| 6,875,843 B2 | 4/2005 | Jacobson |
| 6,949,258 B2 | 9/2005 | Zhang |
| 7,098,305 B2 | 8/2006 | Deghenghi et al. |
| 7,154,002 B1 | 12/2006 | Bressi et al. |
| 7,214,662 B2 | 5/2007 | Sarlikiotis et al. |
| 7,410,957 B2 | 8/2008 | Bauss et al. |
| 7,605,123 B2 | 10/2009 | Radhakrishnan et al. |
| 7,658,938 B2 | 2/2010 | Cumming et al. |
| 7,670,626 B2 | 3/2010 | Clancy et al. |
| 7,704,977 B2 | 4/2010 | Leonard |
| 8,053,429 B2 | 11/2011 | Cumming et al. |
| 8,119,159 B2 | 2/2012 | Cumming et al. |
| 8,323,689 B2 | 12/2012 | Cumming et al. |
| 8,323,690 B2 | 12/2012 | Cumming et al. |
| 2002/0002140 A1 | 1/2002 | Holick et al. |
| 2003/0031757 A1 | 2/2003 | Akashe et al. |
| 2003/0091623 A1* | 5/2003 | Cumming et al. ............ 424/465 |
| 2003/0100509 A1* | 5/2003 | Sarlikiotis et al. ............. 514/15 |
| 2003/0114525 A1 | 6/2003 | Kammer et al. |
| 2003/0139378 A1 | 7/2003 | Daifotis et al. |
| 2003/0166508 A1 | 9/2003 | Zhang |
| 2003/0176397 A1 | 9/2003 | Lichtenberger |
| 2003/0181421 A1 | 9/2003 | Horowitz et al. |
| 2004/0087631 A1 | 5/2004 | Bacopoulos et al. |
| 2004/0147484 A1 | 7/2004 | Boyd et al. |
| 2004/0157799 A1 | 8/2004 | Seaman |
| 2005/0065117 A1 | 3/2005 | Lee |
| 2005/0080075 A1 | 4/2005 | Nichols et al. |
| 2005/0119331 A1 | 6/2005 | Butler et al. |
| 2005/0157799 A1 | 7/2005 | Raman |
| 2005/0163849 A1 | 7/2005 | Wong et al. |
| 2005/0221501 A1 | 10/2005 | Arnot et al. |
| 2005/0232981 A1 | 10/2005 | Ben-Sasson |
| 2006/0018874 A1 | 1/2006 | Radhakrishnan et al. |
| 2006/0135405 A1 | 6/2006 | Rischer et al. |
| 2006/0210639 A1 | 9/2006 | Liversidge et al. |
| 2007/0021357 A1 | 1/2007 | Tobia et al. |
| 2007/0021378 A1 | 1/2007 | Varki et al. |
| 2007/0060509 A1 | 3/2007 | Kanikanti et al. |
| 2007/0077313 A1 | 4/2007 | Krebs et al. |
| 2007/0148228 A1 | 6/2007 | Cumming et al. |
| 2007/0196464 A1 | 8/2007 | Cumming et al. |
| 2007/0212395 A1 | 9/2007 | Donello et al. |
| 2007/0219131 A1 | 9/2007 | Ben-Sasson |
| 2007/0238707 A1 | 10/2007 | Leonard |
| 2007/0292512 A1 | 12/2007 | Leonard et al. |
| 2008/0171848 A1 | 7/2008 | Christiansen et al. |
| 2008/0213366 A1 | 9/2008 | Gowan, Jr. et al. |
| 2008/0275001 A1 | 11/2008 | Cumming et al. |
| 2009/0004281 A1 | 1/2009 | Nghiem et al. |
| 2009/0060861 A1 | 3/2009 | Poulsen |
| 2009/0274758 A1 | 11/2009 | Pinhasi et al. |
| 2009/0280169 A1 | 11/2009 | Leonard |
| 2009/0280170 A1 | 11/2009 | Lee et al. |
| 2010/0022480 A1 | 1/2010 | Leonard |
| 2010/0028421 A1 | 2/2010 | Cumming et al. |
| 2010/0105627 A1 | 4/2010 | Salama et al. |
| 2010/0209499 A1 | 8/2010 | Cumming et al. |
| 2010/0215743 A1 | 8/2010 | Leonard |
| 2010/0247640 A1 | 9/2010 | Leonard |
| 2012/0189692 A1 | 7/2012 | Cullen et al. |

FOREIGN PATENT DOCUMENTS

| | | |
|---|---|---|
| CN | 101125132 | 2/2008 |
| EP | 0370481 A2 | 11/1989 |
| EP | 0376534 | 7/1990 |
| EP | 0497162 | 8/1992 |
| EP | 0517211 | 12/1992 |
| EP | 0580074 | 1/1994 |
| EP | 0747390 A2 | 12/1996 |
| EP | 0667148 | 7/2002 |
| EP | 1246839 | 6/2004 |
| EP | 1674082 A1 | 6/2006 |
| EP | 1339411 | 7/2007 |
| GB | 953626 | 3/1964 |
| GB | 2212396 A | 7/1989 |
| GB | 2336311 A | 10/1999 |
| IE | 1 63119 | 3/1995 |
| JP | S 57-146722 A | 9/1982 |
| JP | 59073600 | 4/1984 |
| JP | S 62-283930 A | 12/1987 |
| JP | 02180837 | 7/1990 |
| JP | 2282327 | 11/1990 |
| JP | 03275633 | 12/1991 |
| JP | 04149126 | 5/1992 |
| JP | 6040949 | 2/1994 |
| JP | 06192107 | 7/1994 |
| JP | 11035458 | 2/1999 |
| JP | 2002537321 | 11/2002 |
| JP | 2004529953 | 9/2004 |
| JP | 2004-533444 A | 11/2004 |
| JP | 2006089496 | 4/2006 |
| RU | 2068689 | 11/1996 |
| WO | WO 84/04674 | 12/1984 |
| WO | WO 93/05903 | 4/1993 |
| WO | WO 93/09785 A1 | 5/1993 |
| WO | WO 93/21907 | 11/1993 |
| WO | WO 94/10983 A1 | 5/1994 |
| WO | WO 95/22319 | 8/1995 |
| WO | WO 95/34294 | 12/1995 |
| WO | WO 97/05903 | 2/1997 |
| WO | WO 97/44017 A1 | 11/1997 |
| WO | WO 98/01159 A2 | 1/1998 |
| WO | WO 99/01579 | 1/1999 |
| WO | WO 99/02120 | 1/1999 |
| WO | WO 99/02485 | 1/1999 |
| WO | WO 99/18972 A1 | 4/1999 |
| WO | WO 99/45934 | 9/1999 |
| WO | WO 00/22909 | 4/2000 |
| WO | WO 00/50012 | 8/2000 |
| WO | WO 00/61111 | 10/2000 |
| WO | WO 01/82903 A1 | 11/2001 |
| WO | WO 01/89479 A2 | 11/2001 |
| WO | WO 01-89479 A2 | 11/2001 |
| WO | WO 02/20037 A1 | 3/2002 |
| WO | WO 02/064148 A2 | 8/2002 |
| WO | WO 02/087597 A1 | 11/2002 |
| WO | WO 02/092069 A1 | 11/2002 |
| WO | WO 02/092070 | 11/2002 |
| WO | WO 03/003999 | 1/2003 |
| WO | WO 03-045419 A1 | 6/2003 |
| WO | WO 03/047493 A2 | 6/2003 |
| WO | WO 03/051373 A1 | 6/2003 |
| WO | WO 03/053401 A2 | 7/2003 |
| WO | WO 03/072123 A1 | 9/2003 |
| WO | WO 2005/055973 A2 | 6/2005 |
| WO | WO 2005/063218 | 7/2005 |

(56) References Cited

FOREIGN PATENT DOCUMENTS

| WO | WO 2005/072747 A1 | 8/2005 |
|----|-------------------|--------|
| WO | WO 2005/115331 A2 | 12/2005 |
| WO | WO 2006-010155 A2 | 1/2006 |
| WO | WO 2006/069641 A1 | 7/2006 |
| WO | WO 2006/097537 A2 | 9/2006 |
| WO | WO 2006/102117 A1 | 9/2006 |
| WO | WO 2006/103657 A1 | 10/2006 |
| WO | WO 2006/116565 A2 | 11/2006 |
| WO | WO 2007/0117706 A2 | 10/2007 |
| WO | WO 2007/124090 A2 | 11/2007 |
| WO | WO 2009/137080 A1 | 11/2009 |
| WO | WO 2010/032140 A2 | 3/2010 |
| WO | WO 2010/099255 A1 | 9/2010 |
| WO | WO 2011/120033 A1 | 9/2011 |

OTHER PUBLICATIONS

Yang et al., Deposition of insulin powders for inhalation in vitro and pharmacodynamic evaluation of absorption promoters in rats, Acta pharmaceutica Sinica 40:1069-1074 (2005).

Zhou et al., "Effects of cholic acid and other enhancers on the bioavailability of Insulin from a subcutaneous site," Int J Pharm. 69:29-41 (1991).

Motlekar, "Oral delivery of low-molecular-weight heparin using sodium caprate as absorption enhancer reaches therapeutic levels," J. Drug Targeting 13(10):573-583 (2005).

Tanaka et al. "Enhancement of intestinal transport of thyrotropin-releasing hormone via a carrier-mediated transport system by chemical modification with lauric acid," Biochim. Biophys. Acta 1283:119-126 (1996).

Yamamoto et al., "Improvement of intestinal absorption of peptide and protein drugs by chemical modification with fatty acids," Nihon Rinsho 56(3):601-607 (1998).

U.S. Appl. No. 11/450,641, filed Jun. 9, 2006; Office Action mailed Nov. 9, 2011.

U.S. Appl. No. 12/172,707, filed Jul. 14, 2008; Office Action mailed Nov. 9, 2011.

U.S. Appl. No. 12/481,952, filed Jun. 10, 2009; Office Action mailed Nov. 23, 2011.

U.S. Appl. No. 12/436,990, filed May 7, 2009; Office Action mailed Oct. 7, 2011.

Choay et al., "Structure-activity relationship in heparin: A synthetic pentasaccharide with high affinity for antithrombin III and eliciting high anti-factor Xa activity," Biochem. Biophys. Res. Commun. 116:492-499 (1983).

Sikora, "Cancer drug development in the post-genomic age," Curr. Sci. 81:549-54 (2001).

Zips et al., "New anticancer agents: In vitro and in vivo evaluation," In vivo 19:108 (2005).

U.S. Appl. No. 12/765,008, filed Apr. 27, 2010; Office Action mailed Aug. 2, 2011.

U.S. Appl. No. 12/481,952, filed Jun. 10, 2009; Office Action mailed Jul. 26, 2011.

European Application No. 09743067.2, filed May 7, 2009; office action mailed May 12, 2011.

U.S. Appl. No. 13/242,601, filed Sep. 23, 2011.

Jiang G et al. GnRH antagonists: a new generation of long acting analogues incorporating p-ureido-phenylalanines at positions 5 and 6. J. Med. Chem. Dec. 14, 2000; 44: 453-467.

Hild SA et al. The ability of a gonadotropin-releasing hormone antagonist, acyline, to prevent irreversible infertility induced by the indenopyridine, CDB-4022, in adult male rats: the role of testosterone. Biology of Reproduction. Mar. 24, 2004; 71: 348-358.

Grohganz H et al. Development and in vitro evaluation of a liposome based implant formulation for the decapeptide cetrorelix. European Journal of Pharmaceutics and Biopharmaceutics. Dec. 18, 2004; 59: 439-448.

Somatostatin. Wikipedia. Printed Mar. 23, 2009. 4 pp.

Octreotide. Wikipedia. Printed Mar. 23, 2009. 3 pp.

International Search Report and Written Opinion, PCT/US2009/002844, mailed Jul. 31, 2009.

Fernandez et al., "Comparative study on digestive lipase activities on the self emulsifying excipient Labrasol®, medium chain glycerides and PEG esters," Biochim. Biophys. Acta 1771:633-640 (2007).

Kajii et al., "Fluorescence study of the membrane-perturbing action of sodium caprylate as related to promotion of drug absorption," J. Pharm. Sci. 77:390-392 (1988).

Lesnyak, "Medicamental methods of treating osteoporosis," Gynecology, vol. 7 (2005); accessed at www.consilium-medicum.com/article/7685.

U.S. Appl. No. 09/510,560, filed Feb. 22, 2000; Office Action mailed Mar. 26, 2001.

U.S. Appl. No. 09/510,560, filed Feb. 22, 2000; Office Action mailed Jul. 15, 2002.

U.S. Appl. No. 09/510,560, filed Feb. 22, 2000; Office Action mailed Oct. 22, 2003.

U.S. Appl. No. 09/510,560, filed Feb. 22, 2000; Office Action mailed Jun. 4, 2004.

U.S. Appl. No. 09/510,560, filed Feb. 22, 2000; Office Action mailed May 18, 2005.

U.S. Appl. No. 09/510,560, filed Feb. 22, 2000; Office Action mailed Nov. 21, 2005.

U.S. Appl. No. 09/510,560, filed Feb. 22, 2000; Office Action mailed Jun. 14, 2006.

U.S. Appl. No. 09/510,560, filed Feb. 22, 2000; Office Action mailed Dec. 15, 2006.

U.S. Appl. No. 09/510,560, filed Feb. 22, 2000; Office Action mailed Aug. 23, 2007.

U.S. Appl. No. 09/510,560, filed Feb. 22, 2000; Office Action mailed Feb. 20, 2008.

U.S. Appl. No. 09/510,560, filed Feb. 22, 2000; Office Action mailed Sep. 17, 2008.

U.S. Appl. No. 09/510,560, filed Feb. 22, 2000; Office Action mailed May 27, 2009.

U.S. Appl. No. 11/400,689, filed: Apr. 7, 2006; Office Action mailed Feb. 12, 2009.

U.S. Appl. No. 11/450,641, filed: Jun. 9, 2006; Office Action mailed Jun. 25, 2009.

U.S. Appl. No. 11/450,641, filed Jun. 9, 2006; Office Action mailed Apr. 14, 2010.

U.S. Appl. No. 12/172,707, filed Jul. 14, 2008; Office Action mailed Jan. 4, 2011.

U.S. Appl. No. 12/172,707, filed Jul. 14, 2008; Office Action mailed Apr. 27, 2011.

U.S. Appl. No. 12/553,196, filed Sep. 3, 2009; Office Action mailed Sep. 24, 2010.

U.S. Appl. No. 12/553,196, filed Sep. 3, 2009; Office Action mailed Mar. 31, 2011.

U.S. Appl. No. 11/733,007, filed Apr. 9, 2007; Office Action mailed Jan. 29, 2009.

U.S. Appl. No. 11/733,007, filed Apr. 9, 2007; Office Action mailed Aug. 17, 2009.

U.S. Appl. No. 11/761,233, filed Jun. 11, 2007; Office Action mailed Sep. 1, 2009.

U.S. Appl. No. 11/761,233, filed Jun. 11, 2007; Office Action mailed Jun. 28, 2010.

U.S. Appl. No. 12/436,990, filed May 7, 2009; Office Action mailed Sep. 14, 2010.

U.S. Appl. No. 12/436,990, filed May 7, 2009; Office Action mailed Mar. 16, 2011.

U.S. Appl. No. 13/073,202, filed Mar. 28, 2011.

U.S. Appl. No. 13/014,156, filed Jan. 26, 2011. Yamamoto et al., "Pulmonary absorption enhancement of peptides by absorption enhancers and protease inhibitors," J Control Release, 41:57-67 (1996).

Bird, "Genetic aspects of Alzheimer disease," Genet. Med. 10:231-239 (2008).

Breddin, "The role of antithrombin agents and Factor Xa-inhibitors in antithrombotic treatment," Turk. J. Haematol. 19:113-120 (2002).

Kalweit et al., "Pulmonary embolism: a frequent cause of acute fatality after lung resection," Eur. J. Cardio-thorac. Surg. 10:242-247 (1996).

Kleinebudde, "Roll compaction/dry granulation: pharmaceutical applications," Eur. J. Pharm. Biopharm. 58:317-326 (2004).

(56) References Cited

OTHER PUBLICATIONS

Tak et al., "The pathogenesis and prevention of joint damage in rheumatoid arthritis," Arthritis Rheumatism 43:2619-2633 (2000).
Wood-Kaczmar et al., "Understanding the molecular causes of Parkinson's disease," Trends Mol. Med. 12:521-528 (2006).
U.S. Appl. No. 13/014,156, filed Jan. 26, 2011; Office Action mailed Jun. 6, 2013.
U.S. Appl. No. 12/712,527, filed Feb. 25, 2010; Office Action mailed May 20, 2013.
U.S. Appl. No. 13/242,601, filed Sep. 23, 2011; Office Action mailed Jun. 4, 2013.
Chinese Application No. 200980116600.1, filed May 7, 2009; office action mailed Jun. 4, 2013.
European Application No. 09743067.2, filed May 7, 2009; office action mailed May 17, 2013.
European Application No. 09743065.6, filed May 7, 2009; office action mailed Apr. 30, 2013.
Mexican Application No. MX/a/2010/012201, filed May 7, 2009; office action mailed Apr. 9, 2013.
Abrahamson et al., "Synthesis and characterization of iron stearate compounds," J. Inorg. Chem. 54:115-130 (1994).
Cosman et al., "Clinical evaluation of novel bisphosphonate dosing regimens in osteoporosis: The role of comparative studies and implications for future studies," Clin. Ther. 29:1116-1127 (2007).
Drummond et al., "Clinical development of histone deacetylase inhibitors as anticancer agents," Annu. Rev. Pharmacol. Toxicol. 45:495-528 (2005).
European Food Safety Authority, "Scientific opinion on the use of ferric sodium EDTA as a source of iron added for nutritional purposes to foods for the general population (including food supplements) and to foods for particular nutritional uses," EFSA J. 8:1414 (2010).
Kishimoto et al., "Efficacy and tolerability of once-weekly administration of 17.5mg risedronate in Japanese patients with involutional osteoporosis: a comparison with 2.5-mg once-daily dosage regimen," J. Bone Miner. Metab. 24:405-413 (2006).
Schnitzer et al., "Therapeutic equivalence of alendronate 70 mg once-weekly and alendronate 10 mg daily in the treatment of osteoporosis," Aging Clin. Exp. Res. 12:1-12 (2000).
Simpson et al., "Significance of non-esterified fatty acids in iron uptake by intestinal brush-border membrane vesicles," Biochim. Biophys. Acta 941:39-47 (1988).
U.S. Appl. No. 12/172,707, filed Jul. 14, 2008; Office Action mailed Feb. 21, 2012.
U.S. Appl. No. 12/768,008, filed Apr. 27, 2010; Office Action mailed Feb. 29, 2012.
U.S. Appl. No. 12/767,076, filed Apr. 26, 2010; Office Action mailed Feb. 9, 2012.
U.S. Appl. No. 12/767,076, filed Apr. 26, 2010; Office Action mailed May 31, 2012.
U.S. Appl. No. 12/712,527, filed Feb. 25, 2010; Office Action mailed Sep. 26, 2012.
U.S. Appl. No. 13/345,185, filed Jan. 6, 2012; Office Action mailed Feb. 13, 2013.
Chinese Application No. 200980116600.1, filed May 7, 2009; office action mailed Nov. 7, 2012.
European Application No. 09743067.2, filed May 7, 2009; office action mailed May 7, 2012.
Chinese Application No. 200980121295.5, filed May 7, 2009; office action mailed Oct. 25, 2012.
Israeli Application No. 209136, filed May 7, 2009; office action mailed Sep. 10, 2012.
U.S. Appl. No. 13/690,082, filed Nov. 30, 2012.
Herbst, "Gonadotropin-releasing hormone antagonists," Curr. Opin. Pharmacol. 3:660-666 (2003).
U.S. Appl. No. 13/345,185, filed Jan. 6, 2012; Office Action mailed Jul. 30, 2013.
Japanese Application No. 2011-508510, filed May 7, 2009; office action mailed Sep. 6, 2013.
Japanese Application No. 2011-508508, filed May 7, 2009; office action mailed Sep. 6, 2013.
Russian Application No. 2010150093, filed May 7, 2009; office action mailed Jun. 7, 2013.
U.S. Appl. No. 13/073,20, filed Mar. 28, 2011; Office Action mailed Oct. 24, 2013.
Australian Application No. 2009244799, filed May 7, 2009; office action mailed Oct. 28, 2013.
Taiwan Application No. 098115182, filed May 7, 2009; office action mailed Oct. 24, 2013.
Allen, "Ansel's Pharmaceutical Dosage Forms and Drug Delivery Systems," 8th Ed., Lippincott Williams & Wilkins, 51-58 (2005).
Anderberg et al., "Sodium Caprate Effects Dilations in Human Intestinal Tight Junctions and Enhances Drug Absorption by the Paracellular Route," Pharm. Res. 10(6):857-864 (1993).
Andriuoli et al., "Heparin by Alternative Routes of Administration", Haemostasis 20:(suppl 1):154-158 (1990).
Appendix A: Webpage publication provided by Lambent Technologies www.petroferm.com/prodinfo.asp?bus=2&mkt=4&app=3, 2006.
Artursson, "Epithelial Transport of Drugs in Cell Culture. I: A Model for Studying the Passive Diffusion of Drugs over Intestinal Absorbtive (Caco-2) Cells," J Pharm Studies 79(7):476-482 (1990).
Aungst, "Structure/effect studies of fatty acid isomers as skin penetration enhancers and skin irritants," Pharm. Res. 6:244-247 (1989).
Aungst et al., "Enhancement of the intestinal absorption of peptides and non-peptides," J. Control. Release 41:19-31 (1996).
Baker et al., "Role of Body Surface Area in Dosing of Investigatioanl Agents in Adults, 1991-2001," J. Natl. Cancer Inst. 94:1883-1888 (2002).
Bennett et al., "Pulmonary Delivery of Detirelex by Intratracheal Instillation and Aerosol Inhalation in the Briefly Anesthetized Dog," Pharm. Res. 11:1048-1054 (1994).
Brayden et al., "Heparin Absorption Across the Intestine: Effects of Sodium N-[8-(2-Hydroxybenzoyl)Amino]Caprylate in Rat In Situ Intestinal Instillations and in Caco-2 Monolayers," Pharm. Res. 14(12):1772-1779 (1997).
Chan et al., "Depsipeptide (FR901228, NSC-630176) pharmacokinetics in the rat by LC/MS/MS," Invest. New Drugs 15:195-206 (1997).
Cumming et al., "In vitro evaluation of a series of sodium carboxylates as dermal penetration enhancers," Int J Pharm 108:141-148 (1994).
Declaration of Dr. Thomas W. Leonard from European Patent Application EP 00905186.3, 2007.
Doluisio et al., "Drug Absorption I: An In Situ Rat Gut Technique Yielding Realistic Absorption Rates," J. Pharm. Studies 58(10):1196-1200 (1969).
Gennaro, "Remington: The Science and Practice of Pharmacy," 19th Edition, Mack Publishing Co., p. 1618 (1995).
Hahn, "Chemotherapy Dose Calculation and Administration in Exotic Animal Species," Sem. Avian Exotic Pet Med. 14:193-198 (2005).
Lambent Technologies, "Technical Data Sheet for Lumulse L-4, Lumulse L-12, and Lumulse L-23", pp. 1-2 (2004).
Lambent Technologies, "Material Safety Data Sheet for Lumulse L-12", pp. 1-3 (2004).
Lindmark et al., "Mechanisms of Absorption Enhancement by Medium Chain Fatty Acids in Intestinal Epithelial Caco-2 Cell Monolayers," J. Pharmacol. Exp. Ther. 275(2):958-964 (1995).
Lindmark et al., "Mechanism of Absorption Enhancement in Humans After Rectal Administration of Ampicillin in Suppositories Containing Sodium Caprate," Pharm. Res. 14(7):930-935 (1997).
Massa et al., "3-(4-Aroyl-1H-pyrrol-2-yl)-N-hydroxy-2-propenamides, a New Class of Synthetic Histone Deacetylase Inhibitors," J. Med. Chem. 44:2069-2072 (2001).
"McGraw-Hill Dictionary of Chemical Terms", McGraw-Hill Book Company Ed. S.P. Parker, New York pp. 208, 209, 251 (1985).
Mechanick et al., "Effect of a Convenient Single 90-mg Pamidronate Dose on Biochemical Markers of Bone Metabolism in Patients With Acute Spinal Cord Injury," J. Spinal Cord Med. 29(4):406-412 (2006).
Moradei et al., "Histone deacetylase inhibitors: Latest developments, trends and prospects," Curr. Med. Chem. 5(5):529-560 (2005).

(56) References Cited

OTHER PUBLICATIONS

Murakami et al., "Effect of Oleic Acid Vesicles on Intestinal Absorption of Carboxyfluorescein in Rats", Pharm. Res. 3(1):35-40 (1986).
Muranishi, "Absorption Enhancers," Crit. Rev. Ther. Drug Carrier Systems 7:1-33 (1990).
Muranushi et al., "The Effects of Fatty Acids and Their Derivatives on the Intestinal Absorption of Insulin in Rat," Drug Dev. Indust. Pharm. 19(8):929-941 (1993).
Oda (Inamori), "Absorption Enhancement of Argatroban by Medium Chain Fatty Acid Sodium Salts," Proceedings Int'l Symp. Control. Rel. Bioact. Mater. 24:283-284 (1997).
Palin et al., "The oral absorption of cefoxitin from oil and emulsion vehicles in rats," Int. J. of Pharmaceutics 33:99-104 (1986).
Poster Presentation entitled "A Phase I Trial and Pharmacokinetic Study of Depsipeptide in Pediatric Patients with Refractory Solid Tumors: A Children's Oncology Group Study" at American Society of Clinical Oncology meeting, May 2005, abstract 8528 (Fouladi et al.).
Sawada et al., "Role of Paracellular Pathway in Nonelectrolyte Permeation Across Rat Colon Epithelium Enhanced by Sodium Caprate and Sodium Caprylate," Pharm. Res. 8(11):1365-1371 (1991).
Sawyer et al., "Body surface area as a determinant of pharmacokinetics and drug dosing," Invest. New Drugs 19:171-177 (2001).
Schneider et al., "Evaluation of drug penetration into human skin ex vivo using branched fatty acids and propylene glycol," Int. J. Pharm. 145:187-196 (1996).
Sinko, "Martin's Physical Pharmacy and Pharmaceutical Sciences," $5^{th\ Ed.}$, Lippincott Williams & Wilkins, 355-357 (2006).
Tomita et al., "Absorption-Enhancing Mechanism of Sodium Caprate and Decanoylcarnitine in Caco-2 Cells," J. Pharmacol. Exp. Ther. 272(2):739-743 (1995).
Tomita et al., "Enhancement of Colonic Drug Absorption by the Transcellular Permeation Route," Pharm. Res. 5(12):786-789 (1988).
Tomita et al., "Enhancement of Colonic Drug Absorption by the Paracellular Permeation Route," Pharm. Res. 5(6):341-346 (1988).
Tomita et al., "Differences in the Enhancing Effects of Sodium Caprate on Colonic and Jejunal Drug Absorption," Pharm. Res. 9(5):648-653 (1992).
WPI Database, Accession No. 1984-142694, English language abstract of JP 59073600.
WPI Database, Accession No. 1992-028863, English language abstract of JP 03275633.
WPI Database, Accession No. 1997-287727, English language abstract of RU 2068689.
Yeh et al., "Effect of Medium-Chain Glycerides on Physiological Properties of Rabbit Intestinal Epithelium in Vitro," Pharm. Res. 11(8):1148-1154 (1994).
Goodnough et al., "Erythropoietin, iron, and erythropoiesis," Blood 96:823-833 (2000).
Hovgaard, "Insulin stabilization and gastrointestinal absorption," Ph.D. thesis, pp. 1-218 (1991).
Maher et al., "Safety and efficacy of sodium caprate in promoting oral drug absorption: from in vitro to the clinic," Adv. Drug Del. Rev. 61:1427-1449 (2009).
Vetter et al., "Development and in vivo availability study of an oral fondaparinux delivery system," Eur. J. Pharm. Sci. 41:489-497 (2010).
U.S. Appl. No. 13/690,082, filed Nov. 30, 2012; Office Action mailed Oct. 29, 2013.
U.S. Appl. No. 12/481,952, filed Jun. 10, 2009; Office Action mailed Apr. 3, 2014.
U.S. Appl. No. 12/767,076, filed Apr. 26, 2010; Office Action mailed Mar. 24, 2014.
U.S. Appl. No. 13/014,156, filed Jan. 26, 2011; Office Action mailed Apr. 11, 2014.
U.S. Appl. No. 12/436,990, filed May 7, 2009; Office Action mailed Mar. 4, 2014.
U.S. Appl. No. 12/436,990, filed May 7, 2009; Office Action mailed Jul. 10, 2014.
U.S. Appl. No. 13/242,601, filed Sep. 23, 2011; Office Action mailed Dec. 17, 2013.
U.S. Appl. No. 13/073,202, filed Mar. 28, 2011; Office Action mailed May 20, 2014.
Chinese Application No. 200980116600.1, filed May 7, 2009; office action mailed Jan. 6, 2014.
Japanese Application No. 2011-508510, filed May 7, 2009; office action mailed Mar. 28, 2014.
Australian Application No. 2009244797, filed May 7, 2009; office action mailed Nov. 15, 2013.
Chinese Application No. 200980121295.5, filed May 7, 2009; office action mailed Jun. 20, 2013.
Chinese Application No. 200980121295.5, filed May 7, 2009; office action mailed Dec. 20, 2013.
European Application No. 09743065.6, filed May 7, 2009; office action mailed Feb. 24, 2014.
Israeli Application No. 209136, filed May 7, 2009; office action mailed Feb. 9, 2014.
Japanese Application No. 2011-508508, filed May 7, 2009; office action mailed Apr. 4, 2014.
Mexican Application No. Mx/a/2010/012201, filed May 7, 2009; office action mailed Nov. 26, 2013.
Mexican Application No. Mx/a/2010/012201, filed May 7, 2009; office action mailed Jun. 17, 2014.
Chinese Office Action corresponding to Chinese Application No. 200980121295.5, issued Sep. 11, 2014.
Office Action corresponding to Canadian Application No. 2,723,558 issued Sep. 4, 2014.

* cited by examiner

Figure 1

| Batch # | T122//165-100 | 2K01067 | XF139//042-30-03 (2K07045) | XF173//315-125 | XF185//165-133 (XF185//315-129) | XF173//315-151A |
|---|---|---|---|---|---|---|
| Final Lyophilization | 10% HOAc/90 % Water | 0.2% HOAc in ACN/Water* ~ 9 mg/mL | 90% HOAc/10% water 45 mg/mL | 30 mg/mL 10% HOAc-10% ACN | 30 mg/mL 10% HOAc-10% ACN | 50 mg/mL 10% HOAc-30% ACN |

Figure 2

| Conc. | Acyline b.No. T122//165-100 | | Acyline b.No. XF139//042-30-03 | | Acyline b.No. 2K01067D | | Acyline b.No. XF173//315-125 | | Acyline b.No. XF185//165-133 | | Acyline b.No. XF173//315-151A | |
|---|---|---|---|---|---|---|---|---|---|---|---|---|
| | 5 mg in 50 mg of PG | 10 mg in 50 mg of PG | 5 mg in 50 mg of PG | 10 mg in 50 mg of PG | 5 mg in 50 mg of PG | 10 mg in 50 mg of PG | 5 mg in 50 mg of PG | 10 mg in 50 mg of PG | 5 mg in 50 mg of PG | 10 mg in 50 mg of PG | 5 mg in 50 mg of PG | 10 mg in 50 mg of PG |
| $T_{0h}$ (freshly made) | Suspension (non viscous) | Suspension (non viscous) | Suspension (non viscous) | Suspension (non viscous) | Suspension (non viscous) | Not available | Suspension (non viscous) | Suspension (non viscous) | Suspension (non viscous) | Suspension (non viscous) | Suspension (non viscous) | Suspension (non viscous) |
| $T_{2h}$ | Clear solution (non viscous) | Not available | Suspension (non viscous) | Not available | Suspension (non viscous) | Not available | Clear solution (non viscous) | Not available | Clear solution (non viscous) | Suspension (non viscous) | Clear solution (non viscous) | Suspension (non viscous) |
| $T_{16h}$ (next day) | Clear solution (non viscous) | Clear solution (non viscous) | Suspension (Partially gelled) | Suspension (Gelled) | Suspension (Gelled) | Not available | Clear solution (non viscous) | Suspension (Gelled) | Clear solution (non viscous) | Suspension (Gelled) | Clear solution (non viscous) | Suspension (Gelled) |
| $T_{32h}$ (2 days) | Not available | Not available | Suspension (Partially gelled) | Suspension (Gelled) | Suspension (Gelled) | Not available | Not available | Not available | Not available | Not available | Not available | Not available |

Figure 3

| Conc. | Acyline b.No. T122//165-100 | | Acyline b.No. XF139//042-30-03 | | Acyline b.No. 2K01067D | | Acyline b.No. XF173//315-125 | | Acyline b.No. XF185//165-133 | | Acyline b.No. XF173//315-151A | |
|---|---|---|---|---|---|---|---|---|---|---|---|---|
| | $T_{0h}$ | $T_{16h}$ | $T_{0h}$ | $T_{16h}$ | $T_{0h}$ | $T_{16h}$ | $T_{0h}$ | $T_{16h}$ | $T_{0h}$ | $T_{16h}$ | $T_{0h}$ | $T_{16h}$ |
| 0.5% | Clear solution | Clear, slightly viscous solution | Opalescent solution | Clear, slightly jelly solution | Almost clear, (slightly opalescent) solution | Almost clear,(slightly opalescent), slightly jelly solution | Clear solution | Clear, slightly viscous solution | Clear solution | Clear, slightly viscous solution | Clear solution | Clear, slightly viscous solution |
| 1.0% | Clear solution | Hazy, slightly viscous solution | Very opalescent solution | Clear, jelly solution | Almost clear (opalescent) solution | Almost clear (slightly opalescent) gel | Clear solution | Opalescent, slightly viscous, solution | Clear solution | Clear, slightly viscous solution | Clear solution | Clear, slightly viscous solution |

Figure 4 a

| Conc. | Acyline b.No. T122//165-100 | | Acyline b.No. XF139//042-30-03 | | Acyline b.No. 2K01067D | | Acyline b.No. XF173//315-125 | | Acyline b.No. XF185//165-133 | | Acyline b.No. XF173//315-151A | |
|---|---|---|---|---|---|---|---|---|---|---|---|---|
| | 5mg in 1g of SM | 10mg in 1g of SM | 5mg in 1g of SM | 10mg in 1g of SM | 5mg in 1g of SM | 10mg in 1g of SM | 5mg in 1g of SM | 10mg in 1g of SM | 5mg in 1g of SM | 10mg in 1g of SM | 5mg in 1g of SM | 10mg in 1g of SM |
| $T_{0h}$ (freshly made) | Not available | Suspension | Suspension | Not available | Not available | Suspension | Not available | Suspension | Suspension | Suspension | Suspension | Suspension |
| $T_{2h}$ | Not available | Suspension | Not available | Not available | Not available | Not available | Not available | Clear (transparent) solution | Not available | Not available | Clear (transparent) solution | Clear (transparent) solution |
| $T_{16h}$ (next day) | Not available | Clear (transparent) solution | Suspension | Not available | Not available | Suspension | Not available | Clear (transparent) solution | Clear (transparent) solution | Clear (transparent) solution – few particles suspended | Clear (transparent) solution | Clear (transparent) solution |
| $T_{32h}$ (2 days) | Not available | Clear (transparent) solution | Suspension | Not available | Not available | Not available | Not available | Clear (transparent) solution | Clear (transparent) solution | Clear (transparent) solution – few particles suspended | Clear (transparent) solution | Clear (transparent) solution |

Figure 4 b

| Standard Microemulsion (SM) - Placebo formula | | | | |
|---|---|---|---|---|
| Ingredients | Chemical Names | mg/per capsule | % in formulation | function |
| Captex 355 EP/NF | caprylic/ capric triglyceride | 55.000 | 5.500 | oil phase |
| Capmul MCM | glyceryl caprate/ caprylate | 550.000 | 55.000 | low HLB surfactant |
| Polysorbate 80 | polyoxyethylene sorbitan monooleate | 150.000 | 15.000 | high HLB surfactant |
| 1,2 -Propylene Glycol Pharma 1) | propylene glycol | 50.000 | 5.000 | aqueous phase |
| Lutrol E 400 | PEG 400 | 195.000 | 19.500 | aqueous phase |
| Total 'capsule filling' weight (mg) | | 1000.000 | 100.000 | N/A |

1) Propylene glycol was replaced with the equivalent amount of glycerine (both have similar solubilising properties)
2) PEG 400 was replaced with the equivalent amount of PEG 300 (both have similar solubilising properties)

Figure 10 a

| Test Item No | Formula | Total dose of Acyline | Excipients (Brand Names) | Excipients (Proprietary Named) | Function | Excipients Amounts per 1 caps /1 tab |
|---|---|---|---|---|---|---|
| Test Item 3 | M1/ 55% Capmul MCM | 5mg | Captex 355 EP/NF | caprylic/ capric triglyceride | oil/part of Oil Phase (Bioenhancer) | 55.000 |
| | | | Capmul MCM | glyceryl caprate/ caprylate | low HLB surfactant (Bioenhancer) | 550.000 |
| | | | Polysorbate 80 | polyoxyethylene sorbitan monooleate | high HLB surfactant | 150.000 |
| | | | Glycerin | glycerin | Solvent /part Aqueous Phase | 50.000 |
| | | | PEG 300 | PEG 300 | Solvent/part of Aqueous Phase | 195.000 |

Capmul MCM_HLB = 5.5, Polysorbate 80_HLB = 15,
Final HLB value of the system: 7.5

Figure 10 b

| Test Item No | Formula | Total dose of Acyline | Excipients (Brand Names) | Excipients (Proprietary Named) | Function | Excipients Amounts per 1 caps /1 tab |
|---|---|---|---|---|---|---|
| Test Item 4 | M2/ 45% Capmul PG-8 | 5mg | Capmul PG-8 | propylene glycol monocaprylate | oil/part of Oil Phase (Bioenhancer) | 455.000 |
| | | | Capmul MCM | glyceryl caprate/ caprylate | low HLB surfactant (Bioenhancer) | 100.000 |
| | | | Polysorbate 80 | polyoxyethylene sorbitan monooleate | high HLB surfactant | 200.000 |
| | | | Glycerin | glycerin | Solvent /part Aqueous Phase | 50.000 |
| | | | PEG 300 | PEG 300 | Solvent/part of Aqueous Phase | 195.000 |

Capmul MCM_HLB = 5.5, Polysorbate 80_HLG = 15,
Final HLB value of the system: 11.8

Figure 10 c

| Test Item No | Formula | Total dose of Acyline | Excipients (Brand Names) | Excipients (Proprietary Named) | Function | Excipients Amounts per 1 caps /1 tab |
|---|---|---|---|---|---|---|
| Test Item 5 | M3/ 55% Capmul MCM C10 | 5mg | Captex 355 EP/NF | caprylic/ capric triglyceride | oil/part of Oil Phase (Bioenhancer) | 55.000 |
| | | | Capmul MCM C10 | glyceryl caprate/ caprylate | low HLB surfactant (Bioenhancer) | 550.000 |
| | | | Polysorbate 80 | polyoxyethylene sorbitan monooleate | high HLB surfactant | 150.000 |
| | | | Glycerin | glycerin | Solvent /part Aqueous Phase | 50.000 |
| | | | PEG 300 | PEG 300 | Solvent/part of Aqueous Phase | 195.000 |

Capmul MCM C10_HLB = 3.5, Polysorbate 80_HLB = 15,
Final HLB value of the system: 5.96

COMPOSITIONS OF GNRH RELATED COMPOUNDS AND PROCESSES OF PREPARATION

RELATED APPLICATIONS

This application claims the benefit under 35 U.S.C. §119 (e) of U.S. Provisional Patent Application Ser. No. 61/051,038, filed May 7, 2008, the disclosures of which is incorporated herein by reference in its entirety.

FIELD OF THE INVENTION

The present invention generally relates to compositions of GnRH related compounds and the process of preparation thereof.

BACKGROUND OF THE INVENTION

Gonadotropin-releasing hormone (GnRH) is a neuroendocrine peptide synthesized in the neurovascular terminals of the hypothalamus. GnRH selectively binds specific receptors on membranes of the anterior pituitary gonadotroph cells to stimulate synthesis and releases of the gonadotropic hormones, luteinizing hormone (LH) and follicle-stimulating hormone (FSH). LH and FSH respectively stimulate gonadal production of sex steroids and gametogenesis. Due to its potential in treating sex hormone-dependent diseases such as prostate, ovarian, and breast cancer, GnRH analogs have received much attention. GnRH analogs can be generally classified as either agonists or antagonists. GnRH agonists stimulate the production of LH and FSH when agonists are used at therapeutic doses. GnRH antagonists competitively block the GnRH receptor to suppress bioactive LH, FSH and the resultant sex hormones.

Because of the therapeutic benefits of GnRH analogs, there is a need to provide pharmaceutical compositions of GnRH analogs that are suitable for oral administration, injectable administration and other forms of administration.

SUMMARY OF THE INVENTION

The present invention provides compositions comprising a therapeutically effective amount of one or more GnRH antagonists, and a sufficient amount of at least one anti-gelling agent to reduce the gelation of the GnRH antagonists. The reduction of gelation may be achieved by carrying out the synthesis and/or isolation of the GnRH antagonist according to the present invention. Alternatively, the reduction of gelation may be accomplished by using the anti-gelling agents described herein in the formulation. In some embodiments, at least one anti-gelling agent is a medium chain fatty acid salt, or an ester, a ether, or a derivative of a medium chain fatty acid and has a carbon chain length of from about 4 to about 20 carbon atoms. In some embodiments, the anti-gelling agent is a surface active agent. In one embodiment, the anti-gelling agent is a salt of a medium chain fatty acid and has a carbon chain length of from about 8 to about 14 carbon atoms. In another embodiment, at least one anti-gelling agent is selected from the group consisting of sodium caprylate, sodium caprate and sodium laurate. In one embodiment, at least one surface active agent is a polysorbate.

According to some embodiments of the present invention, the GnRH antagonist is prepared in the presence of a co-solvent system in a manner such that the incidence of gelation of the GnRH antagonist is reduced. In another embodiment, the co-solvent system comprises water and at least one water-miscible solvent.

In some embodiments, the GnRH antagonist is acyline. In other embodiments, the GnRH antagonist is selected from the group consisting of abarelix, cetrorelix, degarelix, ganirelix, and a pharmaceutically acceptable salt thereof, and a combination thereof.

According to another aspect of the present invention, processes for preparing a GnRH antagonist are provided. The process comprises preparing the GnRH antagonist in the presence of a co-solvent system to reduce the gelation of the GnRH antagonist. In one embodiment, the co-solvent system is used during a final step of the preparation of the GnRH antagonist.

According to some aspects of the present invention, methods for preparation of a composition of one or more GnRH antagonists are provided. The method comprises mixing the GnRH antagonists with one or more anti-gelling agents, wherein at least one anti-gelling agent is a medium chain fatty acid salt, or an ester, an ether, or a derivative of a medium chain fatty acid and has a carbon chain length of from about 4 to about 20 carbon atoms or is a surface active agent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 is a table describing the preparation of different acyline batches.

FIG. 2 shows appearance of 9% and 16.7% acyline samples of different acyline batches in propylene glycol.

FIG. 3 shows the appearance of 0.5% and 1% acyline samples of different acyline batches in water.

FIG. 4(a) shows the appearance of 5 mg and 10 mg doses acyline microemulsions of different acyline batches.

FIG. 4(b) shows the formulation of the microemulsion.

FIG. 10(a) illustrates the formulation of microemulsion 1-55% Capmul MCM. FIG. 10(b) illustrates the formulation of microemulsion 2-45% Capmul PG-8. FIG. 10(c) illustrates the formulation of microemulsion 3-55% Capmul MCM C10.

DETAILED DESCRIPTION

Figure 5:
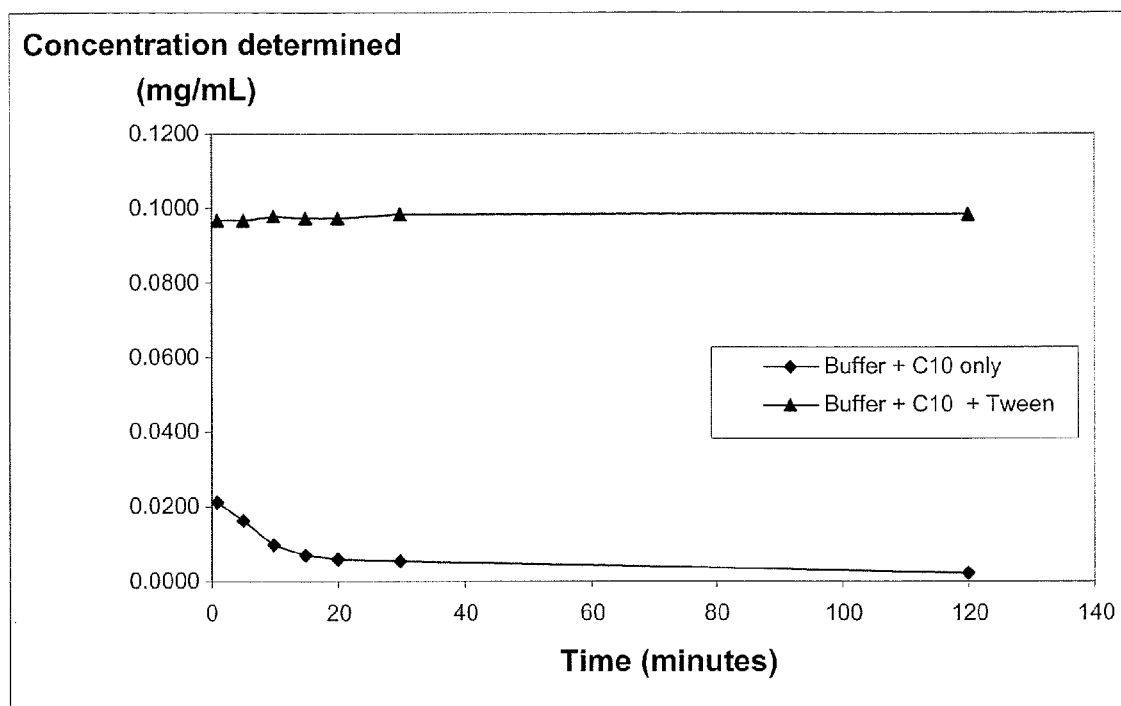
FIG. 5 graphically demonstrates the comparison results of the gelation of 0.1 mg/mL acyline sample with 1% and 0% Tween 80.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

All patents, patent applications and publications referred to herein are incorporated by reference in their entirety. In case of a conflict in terminology, the present specification is controlling.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this invention belongs.

As used herein, "alcohol" means an organic compound in which one or more hydroxyl (OH) groups are attached to carbon (C) atoms in place of hydrogen (H) atoms. In some embodiments, the alcohol contains 1-6 carbon atoms. Yet, in other embodiments, the alcohol contains 1-4 carbon atoms. Exemplary alcohols include, but are not limited to, methanol, ethanol, n-propanol, iso-propanol, butanol, tert-butanol, pentanol, hexanol.

As used herein, "gelation" means that a compound of interest, for example a GnRH related compound, undergoes aggregation to form fibrils, dimers, longer polymers coagulates, or structures that may result in formation of a colloid structure or gel. The viscosity of the mixture, used in the present application, may be applied to a compound of interest in aqueous solution or a solid mass.

"Gelation" may occur to varying extents, and may occur in such a manner as to be non-detectable by ordinary means. For example, there may be no increased viscosity or changes in the flow characteristics of the solution. However, the material formed from the gelation (hereinafter "gel") may be removed by physical means such as filtration and thus detected by analytical techniques known to one skilled in the art. The presence of gels may cause significant problems in the development of different administration forms. For example, when the gelled system is processed to obtain powders of the drug as part of drug substance manufacturing techniques, a xerogel may be formed during the process. As used herein, 'xerogel' is a solid formed from the gel after the liquid is removed from a gelled system. The powder obtained from the gelled system containing xerogel can have substantially different characteristics from powders obtained from solutions that contain no gelled material. In some situations, obtained power loses the biological activity. Therefore, the formation of gels may potentially cause deleterious effects at either the drug substance processing stage, or at the dosage form preparation or storage stage.

The degree of agglomeration or coalescence which results in the formation of the gel may be measured by various methods known to one skilled in the art, for example micro or macro filtration followed by assay of the filtrate, centrifugation followed by assay of the supernatant, or various optical absorption or diffraction methods including those utilizing visible or UV light methods, or laser based methods. The methods of measuring physical characteristics of the liquid may also be used such as surface tension, freezing point depression, viscosity, or measurement of other colligative properties. The degree of xerogel formation may be measured by dispersing the material in water and using the techniques described herein or by direct measurement on the powder by methods known to the art including x-ray powder diffraction, IR spectroscopy, or other methods that may be carried out on powdered materials.

As used herein, the term "reduce the gelation" means to disrupt, retard or eliminate the gel formation of a compound. In situation where the gelation is reversible, the term "reduce the gelation" also means to reverse the gel back to monomeric form of the compound which maintains its biological activity. As used herein, the term "anti-gelling agent" refers to an agent, a compound, a composition or a combination thereof which may inhibit the gelation of at least 50% of the GnRH antagonist, when a sufficient amount of the anti-gelling agent is used. In some embodiments, the anti-gelling agent may inhibit the gelation of at least 80% of the GnRH antagonist, when a sufficient amount of the anti-gelling agent is used. In some embodiments, the anti-gelling may inhibit the gelation of at least 90% of the GnRH antagonist, when a sufficient amount of the anti-gelling agent is used. In some embodiments, the anti-gelling may inhibit the gelation of at least 95% of the GnRH antagonist, when a sufficient amount of the anti-gelling agent is used.

As used herein, a "therapeutically effective" or "therapeutically acceptable" amount refers to an amount that will elicit a therapeutically useful response in a subject. The therapeutically useful response may provide some alleviation, mitigation, or decrease in at least one clinical symptom in the subject. Those skilled in the art will appreciate that the therapeutic useful response need not be complete or curative, as long as some benefit is provided to the subject. In some embodiments, the subject is an animal. In some embodiments, the subject is a human.

As used herein, the term "water miscible solvent" means a solvent that can be mixed with water to form a solution. Water miscible solvents may be used to create a hydrophilic phase.

The present invention provides compositions comprising, consisting essentially of or consisting of, a therapeutically effective amount of one or more GnRH related compounds, and a sufficient amount of at least one anti-gelling agent to reduce the gelation of the GnRH related compound. In some embodiments, in the composition, the gelation of at least 50% of the GnRH related compound is inhibited. In one embodiments, in the composition, the gelation of at least 80% of the GnRH related compound is inhibited. In some embodiments, in the composition, the gelation of at least 90% of the GnRH related compound is inhibited.

The compositions described herein may be used directly for storage, processing or administration. Alternatively, the composition may also be used to mix with a proper medium (e.g. a solvent, a microemulsion or a solid mass) for storage, processing or administration. In the situations where a medium is used, the gelation of GnRH related compound in the medium is reduced as described herein.

In some embodiments, the GnRH related compound is prepared in the presence of a co-solvent system in a manner such that the gelation of the GnRH related compound is reduced.

In some embodiments, at least one anti-gelling agent is a medium chain fatty acid salt, or an ester, an ether, or a derivative of a medium chain fatty acid and has a carbon chain length of from about 4 to about 20 carbon atoms. In some embodiments, at least one the anti-gelling agent is a surface active agent.

In some embodiments, the composition of the present invention is solid at room temperature. In some embodiments, the composition is a pharmaceutical composition in an oral dosage form. Such compositions may allow the GnRH related compound to substantially or completely disperse in a solution from a tablet or a capsule.

In one embodiment, the dissolution rate of the stabilizing agent and the GnRH related compound in the composition are substantially the same.

I. GnRH Related Compounds

The present invention may be applied to a variety of GnRH related compounds which have a tendency of gelation in a solution system. As used herein, the "tendency of gelation" refers to that at least 50% of a compound undergoes aggregation to form fibrils, dimers, polymers that coagulates, or structures that may result in formation of a colloid structure or gel in a system at a certain temperature (e.g. 37° C.) after the system stands for a period of time (e.g. at least about 2 hours). As used herein, GnRH related compounds include both GnRH antagonists and GnRH agonists. In some embodiments, the present invention may be applied to GnRH antagonists. In some embodiments, the present invention may be applied to, but are not limited to, the following GnRH antagonists, acyline (Ac-D2Nal-D4Cpa-D3Pal-Ser4Aph(Ac)-D4Aph(Ac)-Leu-ILys-Pro-DAla-NH2), Acetyl-β-[2-Naphthyl]-D-Ala-D-p-Chloro-Phe-β-[3-Pyridyl]-D-Ala-Ser-Nε-[Nicotinoyl]-Lys-Nε-[Nicotinoyl]-D-Lys-Leu-Nε-[Isopropyl]-Lys-Pro-D-Ala-NH₂ (also referred to herein as Antide), acetyl-D2Nal1, D4C1Phe2, D3Pal3, ARg5, Dglu6 (AA) (also referred to herein as NalGlu), acetyl-D2Nal-D4ClPhe-D3Pal-Ser-Aph(Ac)-D-Aph(Ac)-Leu-Lys(Ipr)-Pro-D-Ala-NH₂, Abarelix (Speciality European Pharma, Dusseldorf, Germany), Nal-Lys, Ganirelix (Orgalutron/Antagon) (Organan, West Orange, N.J.), Cetrorelix I (Aetema Zentaris Inc, Frankfurt, Germany), Cetrotide, Azaline B, new generation long-acting GnRH analogues incorporating p-ureido-phenylalanines at positions 5 and 6 (such as Degarelix), FE200486, Ac-D2Nal-D4Cpa-D3Pal-Ser-4Apb(L-hydroorotyl)-D4Aph(carbarnoyl)-Leu-ILys-Pro-DAla-NH₂ (the acetate salt of which is FE200486), Ac-D2Nal-D4Cpa-D3Pal-Ser-4Aph(Atz)-D4Aph(Atz)-Leu-ILys-Pro-DAla-NH₂ wherein Atz is 3'-amino-1H-1',2',4'-triazol-5'-yl,5, and the antagonists described in U.S. Pat. Nos. 5,506,207, 5,821,230, 5,998,432, 6,156,772, 6,156,767, 6,150,522, 6,150,352, 6,147,088, 6,077,858, 6,077,847, 6,025,366, 6,017,944, 6,004,984, 6,214,798, and 6,875,843. In some embodiments, the GnRH antagonists of the present invention have a tendency of gelation in the presence of ions. In some embodiments, at least one GnRH antagonist is selected from the group consisting of acyline, abarelix, azaline B, cetrorelix, ganirelix, teverelix, degarelix, antide, orntide and GnRH antagonists described in U.S. Pat. No. 7,098,305.

In one embodiment, at least one GnRH antagonist is selected from the group consisting of abarelix, cetrorelix, degarelix, ganirelix, and a pharmaceutically acceptable salt thereof.

As used throughout this specification and claims, the term "abarelix" refers to a compound having a structure of Formula I Formula I

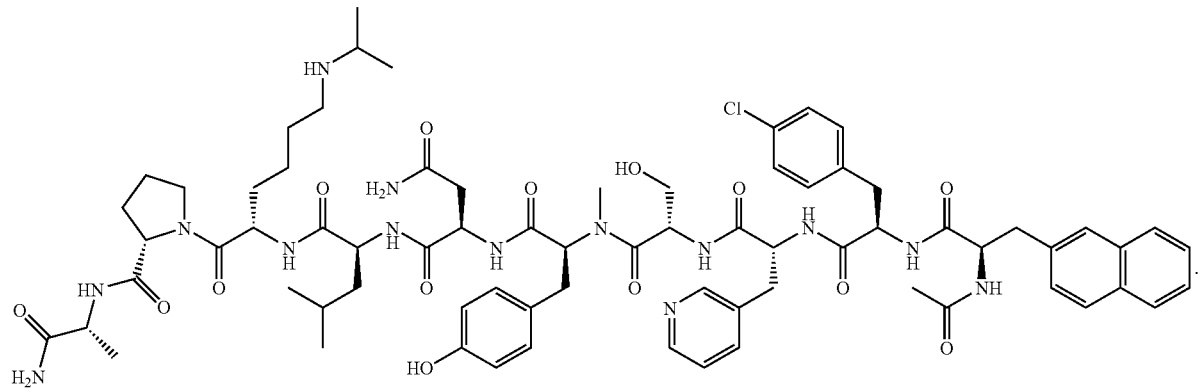

The IUPAC name of Formula I is acetyl-D-β-naphthylalanyl-D-4-chlorophenylalanyl-D-3-pyridylalanyl-L-seryl-L-N-methyl-tyrosyl-D-asparagyl-L-leucyl-L-N(e)-isopropyl-lysyl-L-prolyl-D-alanyl-amide. The term "abarelix" includes the compound of Formula I, pharmaceutically acceptable salts thereof, and equilibrium mixtures of these. The term "abarelix" also includes crystalline, hydrated or solvated crystalline, and amorphous forms of the compound of Formula I and pharmaceutically acceptable salts thereof.

As used throughout this specification and claims, the term "cetrorelix" refers to a compound having a structure of Formula II.

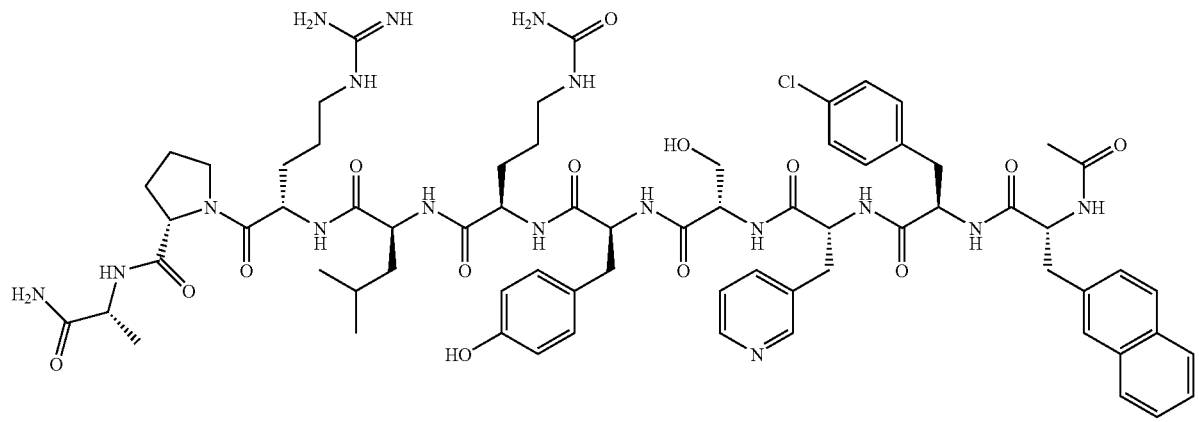

Formula II

The IUPAC name of Formula II is Acetyl-D-3-(2'-naphtyl)-alanine-D-4-chlorophenylalanine-D-3-(3'-pyridyl)-alanine-L-serine-L-tyrosine-D-citruline-L-leucine-L-arginine-L-proline-D-alanine-amide. The term "cetrorelix" includes the compound of Formula II, pharmaceutically acceptable salts thereof, and equilibrium mixtures of these. The term "cetrorelix" also includes crystalline, hydrated or solvated crystalline, and amorphous forms of the compound of Formula II and pharmaceutically acceptable salts thereof.

As used throughout this specification and claims, the term "degarelix" refers to a compound having a structure of Formula III.

The IUPAC name of Formula III is N-acetyl-3-(naphtalen-2-yl)-D-alanyl-4-chloro-D-phenylalanyl-3-(pyridin-3-yl)-D-alanyl-L-seryl-4-((((4S)-2,6-dioxohexahydropyrimidin-4-yl)carbonyl)amino)-L-phenylalanyl-4-(carbamoylamino)-D-phenylalanyl-L-leucyl-N6-(1-methylethyl)-L-lysyl-L-prolyl-D-alaninamide. It is also known as FE-200486. The term "degarelix" includes the compound of Formula III, pharmaceutically acceptable salts thereof, and equilibrium mixtures of these. The term "degarelix" also includes crystalline, hydrated or solvated crystalline, and amorphous forms of the compound of Formula III and pharmaceutically acceptable salts thereof.

Formula III

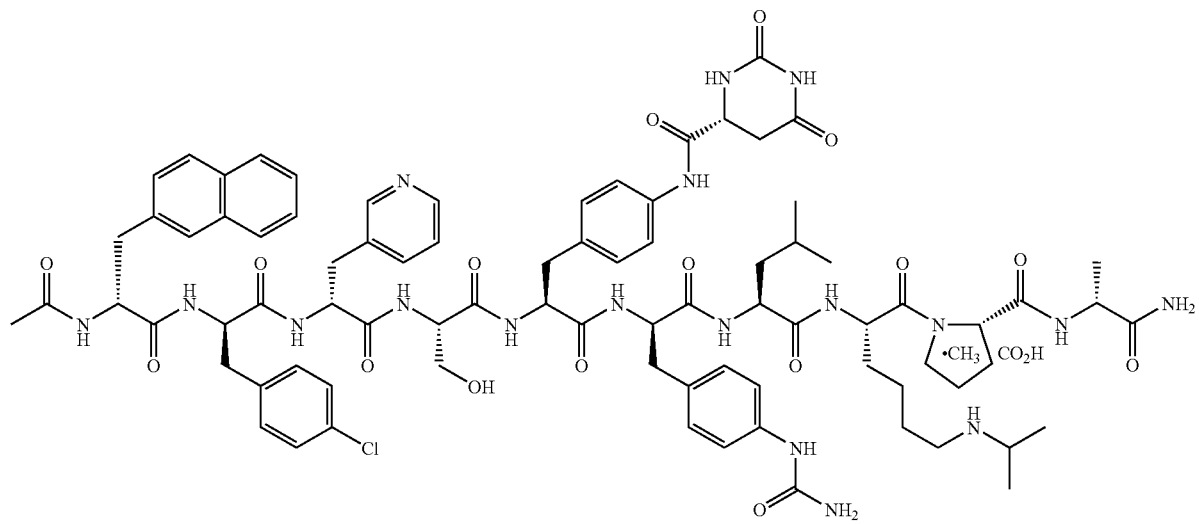

As used throughout this specification and claims, the term "ganirelix" refers to a compound having a structure of Formula IV.

Formula IV

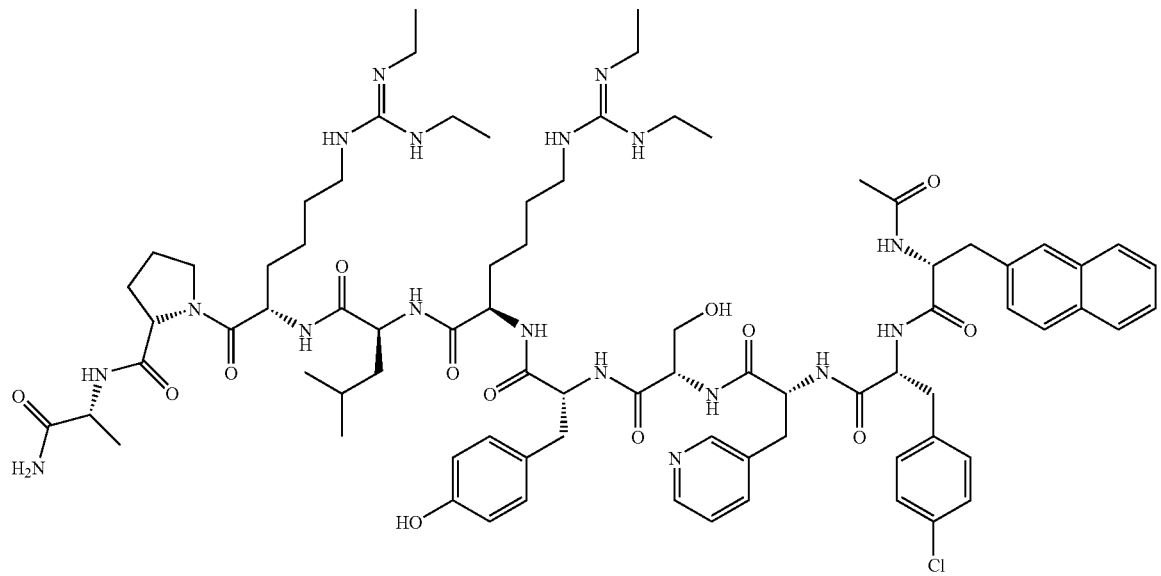

The IUPAC name of Formula IV is a (2S)-1-[(2S)-2-[[(2S)-2-[[(2R)-2-[[(2R)-2-[[(2S)-[[(2R)-2-[[(2R)-2-[[(2R)-2-acetamido-3-naphthalen-2-ylpropanoyl]amino]-3-(4-chlorophenyl)propanoyl]amino]-3-pyridin-3-ylpropanoyl]amino]-3-hydroxypropanoyl]amino]-3-(4-hydroxyphenyl)propanoyl]amino]-6-[bis(ethylamino)methylideneamino]hexanoyl]amino]-4-methylpentanoyl]amino]-6-[bis(ethylamino)methylideneamino]hexanoyl]-N-[(2R)-1-amino-1-oxopropan-2-yl]pyrrolidine-2-carboxamide. The term "ganirelix" includes the compound of Formula IV, pharmaceutically acceptable salts thereof, and equilibrium mixtures of these. The term "ganirelix" also includes crystalline, hydrated or solvated crystalline, and amorphous forms of the compound of Formula IV and pharmaceutically acceptable salts thereof.

In some embodiments, the present invention may be applied to GnRH agonists that exhibit a tendency of gelation. The exemplary GnRH agonists include, but are not limited to, histerelin, leuprolide and goserelin.

The terms "GnRH related compound", "GnRH antagonist" and "GnRH agonist" include all forms thereof including stereoisomers, enantiomers, diastereomers, racemic mixtures, and derivatives thereof, for example, salts, acids, esters and the like. The compound may be provided in any suitable phase state including as solid, liquid, solution, suspension and the like. When provided in a solid particulate form, the particles may be of any suitable size or morphology and may assume one or more crystalline, semi-crystalline and/or amorphous forms.

The GnRH related compounds used in the present invention may be present in any amount which is sufficient to elicit a therapeutic effect and, where applicable, may be present either substantially in the form of one optically pure enantiomer or as a mixture, racemic or otherwise, of enantiomers. As will be appreciated by those skilled in the art, the actual amount of GnRH related compounds used in the composition will depend on the potency of the selected GnRH compound in question.

The GnRH antagonists applied in the present invention can be prepared using a method known to one of ordinary skill in the art or a process described in the present invention. For example, acyline can be prepared according to the method described in U.S. Pat. No. 5,506,207. Alternatively, acyline can be prepared by the process using a co-solvent system described below in section II.

II. Application of Co-Solvent System During the Preparation of a GnRH Related Compound It has been discovered that the method of preparation of an GnRH related compound, may affect the tendency of gelation of the GnRH related compound, for example, optimizing the purification conditions of the final step of the preparation.

One aspect of the invention provides compositions comprising a therapeutically effective amount of a GnRH related compound, wherein the GnRH related compound is prepared in the presence of a co-solvent system in a manner such that the gelation of the GnRH compound is reduced.

Another aspect of the present invention provides processes for preparing a GnRH related compound. The process comprises preparing the GnRH related compound in the presence of a co-solvent system to reduce the gelation of the GnRH related compound.

In some embodiments, the final step of the preparation of the GnRH related compound is conducted in the presence of a co-solvent system. In some embodiments, the final step is drying, using known techniques, such as lyophilization, tray drying, spray drying, fluid bed drying, or other similar techniques known to one skilled in the art.

In some embodiments, the co-solvent system comprises water and at least one water-miscible solvent. The water miscible solvent can be chosen from, but is not limited to, linear or branched $C_{1-6}$ alcohols, tetrahydrofuran, acetone, ethyl methyl ketone, methyl isobutyl ketone, methyl isopropyl ketone, cyclohexanone, diethyl ketone, pentan-3-one, cyclohexane, acetonitrile, N,N-dimethylformamide, N,N-dimethylacetamide, dioxane, alcohol, ethylene glycol, diglyme, monoglyme, ethylene glycol monomethyl ether, diethylene glycol, triethylene glycol, polyethylene glycol and a mixture thereof. In certain embodiments, at least one water miscible solvent is a linear or branched $C_{1-6}$ alcohol. Exemplary suitable alcohols include, but are not limited to, methanol, ethanol, propanol, iso-propanol, butanol, sec-butanol, iso-butanol, tert-butanol, 1-pentanol, 2-pentanol, and hexanol. In some embodiments, at least one water miscible solvent is selected from the group consisting of methanol, ethanol, n-propanol, isopropanol and tert-butanol. In some embodiments, at least one water miscible solvent is selected from the group consisting of methanol, ethanol, iso-propanol, tert-butanol, acetoniltrile and methylene chloride. In some embodiments, the present invention may be carried out with two or more water miscible solvents. In some embodiments, the weight ratio of the water miscible solvent to water is in the range of 1/1000 to 99/1. In some embodiments, the weight ratio is 3/97 to 59/41.

In some embodiments, the process further comprises adding acid during the preparation of the GnRH related compound. Acids used in the present invention include, but are not limited to, acetic acid, sulfuric acid, hydrochloride acid, trifluoracetate, citrate acid, tartaric acid, ascorbic acid, and boric acid, etc. Generally, the concentration of the acid is sufficient to prepare a salt of the GnRH related compound. In some embodiments, the concentration of the acid depends on the molecular weight of the GnRH related compound and the acid used herein. In some embodiments, the concentration is in the range of about 0.5% to about 20% of the solution.

III. Applications of Anti-Gelling Agents in Compositions of GnRH Related Compounds One aspect of the present invention provides compositions comprising a therapeutically effective amount of one or more GnRH related compounds, and a sufficient amount of at least one anti-gelling agent to reduce the gelation of the GnRH related compound.

The amount of the anti-gelling agent used in the present invention can vary considerably. For example, the amount can be dependent upon individual anti-gelling agents, solvent systems and other components in the composition. Generally, the amount of anti-gelling agent should be sufficient to reduce gelation of at least 50% of the GnRH related compound. In some embodiments, the amount of anti-gelling agent should be sufficient to reduce the gelation of at least 80% of the GnRH related compound. In other embodiments, the amount of anti-gelling agent should be sufficient to reduce gelation of at least 90% of the GnRH related compound. In some embodiments, the concentration of the anti-gelling agent in the composition is at least equal or above the CMC (Critical Micelle Concentration) of the anti-gelling agent.

A. Medium Chain Fatty Acid and Derivatives Thereof

In some embodiments, at least one anti-gelling agent is a medium chain fatty acid salt, or ester, ether or a derivative of a medium chain fatty acid and which has a carbon chain length of from 4 to 20 carbon atoms. In some embodiments, at least one anti-gelling agent is medium chain fatty acid salt, or ester, ether or a derivative of a medium chain fatty acid and which has a carbon chain length of from 6 to 20 carbon atoms. In some embodiments, the carbon chain length is from 8 to 14. In some embodiments, at least one anti-gelling agent is a salt of medium chain fatty acid and has a carbon chain length of from 8 to 14 carbon atoms. In some embodiments, at least one anti-gelling agent is a medium chain fatty acid salt, or ester, ether or a derivative of a medium chain fatty acid and which has a carbon chain length of from 6 to 20 carbon atoms; with the provisos that (i) where the anti-gelling agent is an ester of a medium chain fatty acid, said chain length of from 6 to 20 carbon atoms relates to the chain length of the carboxylate moiety, and (ii) where the anti-gelling agent is an ether of a medium chain fatty acid, at least one alkoxy group has a carbon chain length of from 6 to 20 carbon atoms. In another embodiment, at least one anti-gelling agent is a medium chain fatty acid salt, ester, ether or a derivative of a medium chain fatty acid which is solid at room temperature and which has a carbon chain length of from 8 to 14 carbon atoms; with the provisos that (i) where the anti-gelling agent is an ester of a medium chain fatty acid, said chain length of from 8 to 14 carbon atoms relates to the chain length of the carboxylate moiety, and (ii) where the anti-gelling agent is an ether of a medium chain fatty acid, at least one alkoxy group has a carbon chain length of from 8 to 14 carbon atoms. In some embodiments, at least one anti-gelling agent is a sodium salt of a medium chain fatty acid, the medium chain fatty acid having a carbon chain length of from 8 to 14 carbon atoms. In some embodiments, the anti-gelling agent is solid at room temperature. In another embodiment, at least one anti-gelling agent is selected from the group consisting of sodium caprylate, sodium caprate, sodium laurate, and a combination thereof. In one embodiment, at least one anti-gelling agent is sodium caprate.

B. Surface Active Agents

In some embodiments, at least one anti-gelling agent is a surface active agent. As used herein, the term "surface active agent" refers to an agent that lowers the surface tension of the medium in which it is dissolved and/or the interfacial tension with other phases, and, accordingly, is positively adsorbed at the liquid/vapor and/or at other interfaces. The surface active agents employed in the present invention include both ionic agents, i.e., cationic, anionic or zwitterionic, and non-ionic agents, or a mixture thereof.

Examples of cationic surface active agents include, but are not limited to, benzalkonium chloride, dicetyl ammonium chloride, cetyldimethylethylammonium bromide, cetylpyridinium chloride and salts of the above surface active agents.

Examples of anionic surface active agents include, but are not limited to, sodium stearoyl lactylate, hydrogenated lecithin, sodium lauryl sulfate, $C_{8-32}$ fatty acids and salts thereof; cholic acid and derivatives thereof such as deoxycholate, and its salts, ursodeoxycholic acid, and taurocholic acid; $C_{8-56}$ diesters of tartaric acid; phospholipids such as phosphatidic acid and phosphatidyl serine; $C_{5-29}$ monoesters of lactic acid; $C_{8-20}$ sulfonates, including alkyl-, olefin-, and alkylaryl derivatives; tridecyl- and dodecylbenzene sulfonic acids; and $C_{5-33}$ sarcosine and betaine derivatives.

Examples of zwitterionic surface active agents include, but are not limited to, phospholipids such as lecithin, phosphatidylethanolamine, sphingomyelins, dodecyl betaine, dodecyl dimethylamine oxide, cocamidopropyl betaine, and coco ampho glycinate.

Examples of non-ionic surface active agents include, but are not limited to, steareths; polyethylene glycol (PEGs); polysorbates (e.g. Tween 80); cetearyl glucoside; various commercially available sorbitans and their derivatives, for example, sorbitan hexastearate ethoxylate EO 6 mole, sorbitan isostearate, sorbitan laurate, sorbitan monoisostearate ethoxylate EO 20 mole, sorbitan monolaurate ethoxylate EO 20 mole, sorbitan monooleate ethoxylate EO 20 mole, sorbitan monopalmitate ethoxylate EO 20 mole, sorbitan monostearate ethoxylate EO 20 mole, sorbitan monstearate ethoxylate EO 6 mole, Sorbitan oleate, sorbitan palmitate, sorbitan sesquioleate, sorbitan stearate, sorbitan tetraoleate ethoxylate LO 30 mole, sorbitan tetraoleate ethoxylate EO 40 mole, sorbitan tetraoleate ethoxylate EO 6 mole, sorbitan tetrastearate ethoxylate EO 60 mole, sorbitan trioleate ethoxylate EO 20 mole, sorbitan trioleate, sorbitan tristearate ethoxylate EO 20 mole, and sorbitan tristearate; ethoxylated castor oil, $C_{5-29}$ mono-glycerides and ethoxylated derivatives thereof; $C_{15-60}$ diglycerides and polyoxyethylene derivatives thereof having 1 to 90 POE groups; $C_{10-40}$ esters (10-40 carbon atoms in the alcohol) of long chain fatty acids (fatty acids having 16 carbon atoms and above); $C_{10-40}$ alcohols; sterols such as cholesterol, ergosterol, and $C_{2-24}$ esters thereof; $C_{8-96}$ ethoxylated fatty esters; $C_{14-130}$ sucrose fatty esters; and polyoxyethylene (POE) derivatives thereof having 0 to 90 POE groups, e.g., polyoxyethylene sorbitan monooleate, sorbitol hexaoleate POE (50).

In some embodiments, at least one surface active agent is selected from the group consisting of sodium lauryl sulfate, polysorbate surface active agents (such as polysorbate 20 (Tween 20), polysorbate 80 (Tween 80)), sorbitan surface active agents, sorbitan monolaurate and polyethoxylated castor oil and a combination thereof. In some embodiments, at least one surface active agent comprises polysorbate.

IV. Additional Excipients

According to some aspects of the present invention, the composition of the present invention further comprises one or more excipients. As will be appreciated by those skilled in the art, the exact choice of excipients and their relative amounts will depend to some extent on the final dosage form. In some embodiments, the excipients are selected from the group consisting of rate-controlling polymeric materials, diluents, lubricants, disintegrants, plasticizers, anti-tack agents, opacifying agents, pigments, and flavorings.

As used herein, the term "rate controlling polymer material" comprises hydrophilic polymers, hydrophobic polymers and mixtures of hydrophilic and/or hydrophobic polymers that are capable of controlling or retarding the release of the drug compound such as a GnRH related compound from a solid oral dosage form of the present invention. Suitable rate controlling polymer materials include those selected from the group consisting of hydroxyalkyl cellulose such as hydroxypropyl cellulose and hydroxypropyl methyl cellulose; poly(ethylene) oxide; alkyl cellulose such as ethyl cellulose and methyl cellulose; carboxymethyl cellulose, hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly(alkylmethacrylate) and poly (vinyl acetate). Other suitable hydrophobic polymers include polymers and/or copolymers derived from acrylic or methacrylic acid and their respective esters, zein, waxes, shellac and hydrogenated vegetable oils. In one embodiment, the rate-controlling polymer comprises a polymer derived from acrylic or methacrylic acid and their respective esters or copolymers derived from acrylic or methacrylic acid and their respective esters. In another embodiment, the rate-controlling polymer comprises hydroxypropylmethylcellulose (HPMC).

In some embodiments, at least one rate controlling polymer material is selected from the group consisting of poly acrylic acid, poly acrylate, poly methacrylic acid and poly methacrylate polymers such as those sold under the Eudragit® trade name (Rohm GmbH, Darmstadt, Germany), for example, Eudragit® L, Eudragit® S, Eudragit® RL, Eudragit® RS coating materials and mixtures thereof. Some of these polymers can be used as delayed release polymers to control the site where the drug is released. In some embodiments, the rate controlling polymer include polymethacrylate polymers such as those sold under the Eudragit® trade name (Rohm GmbH, Darmstadt, Germany), for example, Eudragit® L, Eudragit® S, Eudragit® RL, Eudragit® RS coating materials and mixtures thereof.

In some embodiments, the present invention may further comprise diluents. Any suitable diluent may be used in the present invention. Exemplary diluents include, but are not limited to, pharmaceutically acceptable inert fillers such as microcrystalline cellulose, lactose, dibasic calcium phosphate, saccharides, and/or mixtures thereof. Examples of diluents include microcrystalline cellulose such as those sold under the Avicel trademark (FMC Corp., Philadelphia, Pa.), for example, Avicel™ pH101, Avicel™ pH102 and Avicel™ pH112; lactose such as lactose monohydrate, lactose anhydrous and Pharmatose DCL21; dibasic calcium phosphate such as Emcompress® (JRS Pharma, Patterson, N.Y.); mannitol; starch; sorbitol; sucrose; and glucose. In some embodiments, the inert filler comprises microcrystalline cellulose. In one embodiment, the inert filler comprises a lactose selected from the group consisting of lactose monohydrate and lactose anhydrous. In another embodiment, the inert filler comprises a saccharide selected from the group consisting of mannitol, starch, sorbitol, sucrose, and glucose. In one embodiment, the saccharide is sorbitol.

In some embodiments, the composition of the present invention may further comprise lubricants. Any suitable lubricant may be used in the present invention. In some embodiments, the lubricant comprises agents that act on the flowability of the powder to be compressed. Exemplary lubricants include, but are not limited to, colloidal silicon dioxide such as Aerosil™ 200, talc, stearic acid, magnesium stearate, and calcium stearate. In some embodiments, the lubricant is stearic acid.

In some embodiments, the composition of the present invention may further comprise disintegrants. Any suitable disintegrant may be used in the present invention. Exemplary disintegrants include, but are not limited to, lightly cross-linked polyvinyl pyrrolidone, corn starch, potato starch, maize starch and modified starches, croscarmellose sodium, cross-povidone, sodium starch glycolate and combinations and mixtures thereof. In some embodiments, the disintegrant is chosen from crospovidone and polyvinylpyrrolidone.

In some embodiments, the composition described above may further comprise an enhancer. The enhancer can be any suitable enhancer that is known to one of ordinary skill in the art. Exemplary enhancers including, but are not limited to, a medium chain fatty acid salt, ester, ether or a derivative of a medium chain fatty acid which has a carbon chain length of from 4 to 20 carbon atoms. In some embodiments, the enhancer is solid at room temperature. In some embodiments, the enhancer is medium chain fatty acid salt, ester, ether or a derivative of a medium chain fatty acid and which has a carbon chain length of from 6 to 20 carbon atoms. In some embodiments, the carbon chain length is from 8 to 14. In some embodiments, the enhancers are S-Cyclodextrins, vitamin E TPGS, gallic acid esters, crospovidones, sorbitan esters, poloxamers, or cremaphors. In some embodiments, the enhancers are medium chain glycerides or a mixture of medium chain glycerides. Exemplary enhancers are further described in U.S. Patent Publication No. 2003/0091623, and U.S. Pat. No. 6,372,728 which are incorporated by reference in their entireties.

V. Methods of Preparing the Compositions of GnRH Related Compound

According to some aspects of the present invention, methods for preparation of a composition of one or more GnRH related compounds are provided. In some embodiments, the method comprises mixing the GnRH related compound with one or more anti-gelling agents. In some embodiments, at least one anti-gelling agent is a medium chain fatty acid salt, or an ester, an ether, or a derivative of a medium chain fatty acid and has a carbon chain length of from about 4 to about 20 carbon atoms or a surface active agent. As used herein, the term "mixing" means contacting, combining, reacting, and/or coating a GnRH antagonist with one or more anti-gelling agents. In one embodiment, "mixing" means combining a GnRH related compound with the anti-gelling agent in a composition. In one embodiment, the concentration of the anti-gelling agent in the composition is at least equal to or above the critical micelle concentration of the anti-gelling agent in the composition. In one embodiment, the GnRH related compound is prepared in the presence of a co-solvent system described herein.

VI. Pharmaceutical Compositions and Administration

In one embodiment, the present invention provides a pharmaceutical composition comprising a therapeutically effective amount of one or more GnRH antagonists, and a sufficient amount of at least one anti-gelling agents to reduce the gelation of the GnRH antagonist, wherein at least one anti-gelling agent is a medium chain fatty acid salt, an ester, an ether, or a derivative of a medium chain fatty acid and has a carbon chain length of from about 4 to about 20 carbon atoms or a surface active agent. In another embodiment, the pharmaceutical composition further comprises a pharmaceutically acceptable carrier. The term "pharmaceutically acceptable carrier" as used herein refers to any substance, not itself a therapeutic agent, used as a vehicle for delivery of a therapeutic agent to a subject.

The compositions of the present invention may be suitable for formulation for oral, parenteral, inhalation spray, topical, rectal, nasal, sublingual, buccal, vaginal or implanted reservoir administration, etc. In one embodiment, the compositions are administered orally, topically, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

In some embodiments, the composition used in the present invention is in an oral dosage form. In some embodiments, the oral dosage form is chosen from tablets, capsules, granules, powders, capsules filled with granules or powders, capsules filled with liquids or semi-solids, sachets filled with granules or powders, liquid, emulsions, microemulsions, and any composition that is capable of forming emulsions. In one embodiment, the oral dosage form may be a tablet, a multiparticulate, or a capsule.

In some embodiments, the oral dosage form is a delayed release dosage form which minimizes the release of the GnRH related compounds and the anti-gelling agents or the enhancer in the stomach, and hence the dilution of the local anti-gelling agent or the concentration of the enhancer therein, and releases the GnRH related compounds and the anti-gelling agent or the enhancer in the intestine. In some embodiments, the oral dosage form is a delayed release rapid onset dosage form. Such a dosage form minimizes the release of GnRH related compound and anti-gelling agent or enhancer in the stomach, and hence the dilution of the local anti-gelling agent or enhancer concentration therein, but releases the GnRH related compound and the anti-gelling agent or the enhancer rapidly once the appropriate site in the intestine has been reached, maximizing the delivery of the poorly permeable or soluble GnRH related compound by maximizing the local concentration of the GnRH related compound and the anti-gelling agent at the site of absorption.

In the case of any of the embodiments described herein, a controlled release coating may be applied to the final dosage form (capsule, tablet, multilayer tablet etc.). In one embodiment, the controlled release coating may comprise a rate controlling polymer material described herein. The dissolution characteristics of such a coating material may be pH dependent or independent of pH.

In some embodiments, the composition of the present invention may have an enteric coating thereon. In one embodiment, the enteric coating comprises a polymer selected from the group consisting of poly(acrylic acid), polyacrylate, poly(methacrylic acid), polymethacrylate, and mixtures thereof. In some embodiments, the enteric coated composition may be in the form of a tablet or capsule.

The term "tablet" as used herein includes, but is not limited to, immediate release (IR) tablets, sustained release (SR) tablets, matrix tablets, multilayer tablets, multilayer matrix tablets, extended release tablets, delayed release tablets and pulsed release tablets any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms that may be useful in the practice of the invention include those selected from the group consisting of IR tablets, SR tablets, coated IR tablets, matrix tablets, coated matrix tablets, multilayer tablets, coated multilayer tablets, multilayer matrix tablets and coated multilayer matrix tablets. In some embodiments, a tablet dosage form is an enteric-coated tablet dosage form. In some embodiments, a tablet dosage form is an enteric-coated rapid onset tablet dosage form.

Capsule solid oral dosage forms that may be useful in the practice of the present invention include those selected from the group consisting of instant release capsules, sustained release capsules, coated instant release capsules, and coated sustained release capsules including delayed release capsules. Capsules may be filled with powders, granules, multi particulates, tablets, semi-solids, or liquids. In some embodiments, a capsule dosage form is an enteric-coated capsule dosage form. In some embodiments, a capsule dosage form is an enteric-coated rapid onset capsule dosage form. Capsules may be made of hard gelatin, soft gelatin, starch, cellulose polymers, or other materials as known to the art.

The term "multiparticulate" as used herein means a plurality of discrete particles, pellets, mini-tablets and mixtures or combinations thereof. If the oral form is a multiparticulate capsule, such hard or soft gelatin capsules can suitably be used to contain the multiparticulate. In some embodiments, a sachet may suitably be used to contain the multiparticulate. In some embodiments, the multiparticulate may be coated with a layer containing rate controlling polymer material. In some embodiments, a multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

In some embodiments, the multiparticulate and one or more auxiliary excipient materials can be compressed into tablet form such as a multilayer tablet. In some embodiments, a multilayer tablet may comprise two layers containing the same or different levels of the same active ingredient having the same or different release characteristics. In some embodiments, a multilayer tablet may contain different active ingredient in each layer. Such a tablet, either single layered or multilayered, can optionally be coated with a controlled release polymer so as to provide additional controlled release properties. In some embodiments, a multiparticulate dosage form comprises a capsule containing delayed release rapid onset minitablets. In some embodiments, a multiparticulate dosage form comprises a delayed release capsule comprising instant release minitablets. In some embodiments, a multiparticulate dosage form comprises a capsule comprising delayed release granules. In some embodiments, a multiparticulate dosage form comprises a delayed release capsule comprising instant release granules.

The term "emulsion" as used herein means a suspension or dispersion of one liquid within a second immiscible liquid. In some embodiments, the emulsion is an oil-in-water or water-in-oil-in-water emulsion.

The term, "microemulsion" as used herein means a solution in which the hydrophobic (oil-like) phase and the hydrophilic (water-like) phase and a surface active agent form micelle structures. Such dispersions are clear and stable over time.

In addition, "emulsion" or "microemulsion", as used herein includes a hydrophilic or a hydrophobic liquid which, on dilution with a hydrophobic or a hydrophilic liquid, respectively, forms an emulsion or a microemulsion. In some embodiments, "emulsion", or "microemulsion", as used herein may include solid or semi-solid materials which may be liquid at higher temperatures. For example, the material may be solid at room temperature. At about body temperature (about 37° C.), the material may be liquid.

Alternatively, pharmaceutically acceptable compositions of this invention may be in the form of a suppository for rectal administration. The suppositories can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of the present invention may be in the form of a topical solution, ointment, or cream in which the active component is suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Where the topical formulation is in the form of an ointment or cream, suitable carriers include, but are not limited to, mineral oil, sorbitan monostearate, polysorbate 60, cetyl esters wax, cetearyl alcohol, 2 octyldodecanol, benzyl alcohol and water.

When the pharmaceutically acceptable composition is an ophthalmic formulation, it may be a micronized suspension in isotonic, pH adjusted sterile aqueous solution, or as a solution in isotonic, pH adjusted sterile saline, either with or without a preservative such as benzylalkonium chloride. Alternatively, for ophthalmic uses, the pharmaceutically acceptable compositions may be formulated in the form of an ointment.

The pharmaceutically acceptable compositions of this invention may also be administered by nasal, aerosol or by inhalation administration routes. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

It should also be understood that a specific dosage and treatment regimen for any particular patient will depend upon a variety of factors, including the activity of the specific compound employed, the age, body weight, general health, gender, diet, time of administration, rate of excretion, drug combination, and the judgment of the treating physician and the severity of the particular disease being treated. The amount of a compound of the present invention in the composition will also depend upon the particular compound in the composition.

VII. Emulsion Compositions

According to some aspects of the present invention, the composition described herein is in the form of an emulsion composition. The GnRH related compound may be contained in an internal phase of the emulsion composition. The non-aqueous, internal phase of the emulsion composition is a polar, pharmaceutically-acceptable oxygen-containing liquid such as $C_2$-$C_{30}$ polyhydric alcohols, poly(ethylene or propylene) glycols with 4-200 repeating units, and the $C_1$-$C_5$ ether or $C_2$-$C_{30}$ ester derivatives of any of the foregoing. Examples of such materials include, but are not limited to, glycerin, propylene glycol, polyethylene glycol 200, 400, 600, 1500, 4000 and 6000 with the number correlating approximately with the number of repeating units and ranging from 4 to 200, ethylene glycol dimethyl ether, tetraethylene glycol dimethyl ether, triacetin, medium chain ($C_6$-$C_{10}$) triglycerides such as tricaprylin (caprylic acid ester of glycerol, and propylene glycol $C_8$ diester (Captex 200). In some embodiments, the emulsion composition comprises as an internal phase, a GnRH related compound contained in a polar, nonaqueous oxygen-containing, pharmaceutically acceptable liquid chosen from glycerin, propylene glycol, polyethylene glycol 200, 400, 600, 1500, 4000 and 6000, ethylene glycol dimethyl ether, tetraethylene glycol dimethyl ether, triacetin, medium chain ($C_8$-$C_{10}$) triglycerides and propylene glycol $C_8$ diester, said internal phase being dispersed in a lower alkyl ester of a $C_8$-$C_{22}$ fatty acid external phase, and lecithin as emulsifying agent, the amounts of the components being polar liquid, 1-20%; fatty ester, 33-70%; and lecithin 20-60%. The emulsion composition is further described in U.S. Pat. No. 5,110,606, which is incorporated by reference in its entirety.

In some embodiments, the composition described herein is in the form of a highly stable water-in-oil microemulsion. The microemulsion comprising a therapeutically effective amount of a GnRH related compound in its internal aqueous phase. The GnRH related compound may be controllably released when needed just prior to administration by using the ready conversion of the microemulsion into an oil-in-water emulsion by adding water to form a continuous aqueous phase. In some embodiments, the water-in-oil microemulsion composition comprises (a) up to about 20 volume percent of an internal dispersed aqueous phase comprising an effective amount of GnRH related compound, (b) from about 30 to 99 volume percent of a continuous oil phase comprising diesters of propylene glycol having from about 15 to 40 carbon atoms, and (c) from about 1 to 70 volume percent of a surface active agent or mixture of surface active agents. In some embodiments, the surface active agent or surface active agent mixture has a hydrophilic-lipophilic balance value of from 7 to 14. The surface active agent or mixture of surface active agents is chosen from cetyldimethylethylammonium bromide, cetylpyridinium chloride; $C_{8-32}$ fatty acids and salts thereof; cholic acid; $C_{8-56}$ diesters of tartaric acid; phospholipids; $C_{5-29}$ monoesters of lactic acid; $C_{8-20}$ sulfonates; tridecyl- and dodecylbenzene sulfonic acids; $C_{5-33}$ sarcosine and betaine; phosphatidylethanolamine, sphingomyelins, ethoxylated castor oil; $C_{5-29}$ monoglycerides and ethoxylated derivatives thereof; $C_{15-60}$ diglycerides and polyoxyethylene derivatives thereof having 1 to 90 POE groups; $C_{10-40}$ esters of long chain fatty acids; $C_{10-40}$ alcohols; $C_{8-96}$ ethoxylated fatty esters; $C_{14-130}$ sucrose fatty esters; and $C_{20-130}$ sorbitol and sorbitan monoesters, diesters, and trimesters, and polyoxyethylene (POE) derivatives thereof having 1 to 90 POE groups. The microemulsion composition is further described in U.S. Pat. No. 5,444,041, which is incorporated by reference in its entirety.

In some embodiments, the composition described herein is in a form of water-in-oil microemulsion composition further comprises (a) up to about 60 volume percent of an internal dispersed aqueous phase comprising an therapeutically effective amount of a GnRH related compound; (b) from about 5 to 99 volume percent of a continuous oil phase comprising at least one pharmaceutically-acceptable oil comprising a $C_{9-83}$ triglyceride, a $C_{7-55}$ diester of propylene glycol, or mixtures thereof; and (c) from about 1 to about 70 volume percent of a surface active agent. In some embodiments, the surface active agent mixture comprises a $C_8$ fatty acid salt. In some embodiments, the surface active agent or surface active agent mixture has an HLB value of at least about 7. The microemulsion composition is further described in U.S. Pat. No. 5,633,226, which is incorporated by reference in its entirety.

In some embodiments, the composition described herein is in a water-in-oil microemulsion composition, comprising 1) up to about 60 volume percent, based upon the total volume of the microemulsion, of an internally dispersed aqueous phase comprising a therapeutically effect amount of a GnRH related compound, (2) from about 5 to 90 volume percent of a continuous oil phase comprising at least one pharmaceutically-acceptable oil; and (3) from 1 to 70 volume percent of a surface active agent or mixture of surface active agents. In some embodiments, the surface active agent or surface active agent mixture has a hydrophilic-lipophilic balance value of from 7 to 14. The microemulsion composition is further described in U.S. Pat. No. 5,646,109 which is incorporated by reference in its entirety.

In another embodiment, the composition described herein may be in a water-in-oil microemulsion composition comprising (a) from about 5 to about 99 volume percent of an oil phase comprising at least one pharmaceutically acceptable oil; (b) up to about 60 volume percent of an aqueous phase comprising water; (c) a therapeutically effective amount of a GnRH related compound; (d) from about 1 to about 70 volume percent of a mixture of surface active agents. In some embodiments, the surface active agents have a combined HLB value of from about 7 to about 14. In some embodiments, the surface active agents comprise (i) a low HLB surface active agent having an HLB below 8, said low HLB surface active agent being at least 80 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surface active agent having an HLB value above about 8. In some embodiments, the microemulsion composition comprises (a) from about 5 to about 99 volume percent of an oil phase comprising at least one pharmaceutically acceptable oil; (b) up to about 60 volume percent of an aqueous phase comprising water; (c) a therapeutically effective amount of a GnRH related compound that has a water:oil partition coefficient greater than 10:1; (d) from about 1 to about 70 volume percent of a mixture of surface active agents and (e) a modifier, present in an amount sufficient to cause the water-in-oil microemulsion to convert to an oil-in-water microemulsion upon the addition of aqueous fluid. In some embodiments, the surface active agents have a combined HLB value of greater than about 7. In other embodiments, the surface active agents comprise (i) a low HLB surface active agent having an HLB below 8, said low HLB surface active agent being at least 80 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surface active agent having an HLB value above about 8. The microemulsion composition is further described in U.S. Pat. No. 5,688,761 which is incorporated by reference in its entirety.

In another embodiment, the composition described herein may be in a stable transparent drug delivery composition. The composition comprises (a) a delivery composition comprising: (1) from about 1 to about 80 weight percent of a pharmaceutically acceptable oil phase; (2) from about 3 to about 98 weight percent surface active agent; (3) from about 2 to about 60 weight percent polyethylene glycol; (4) from about 0.5 to about 15 weight percent water; and (b) a therapeutically effective amount of the GnRH related compound. In some embodiments, the ratio of the polyethylene glycol to water is at least 2:1. In some embodiments, the composition comprises (a) from about 5 to about 70 weight percent of a pharmaceutically acceptable oil phase; (b) from about 10 to about 80 weight percent surface active agent; (c) from about 5 to about 60 weight percent of an aqueous phase comprising from about 60 to about 95 weight percent polyethylene glycol, from about 2 to about 30 weight percent water, and from about 1 to about 15 weight percent plasticizer comprising sorbitol, mannitol, glycerin, sucrose, fructose, glucose, or lactose; and (d) a therapeutically effective amount of the GnRH related compound. The microemulsion composition is further described in U.S. Pat. No. 5,707,648, which is incorporated by reference in its entirety.

VIII Methods of Treatment and Use

Another aspect of the present invention provides a method of treatment of a medical condition treatable by a GnRH related compound comprising administering to a patient suffering from said condition a pharmaceutical composition described herein. As used herein, the medical condition includes, but is not limited to, sex hormone dependent disease such as benign prostate hyperplasia, prostate cancer, estrogen-dependent breast cancer, endometrial cancer, ovarian cancer, endometriosis and precocious puberty, and contraception in a human or animal subject. Yet, according to another aspect of the invention, the pharmaceutical composition as described herein in the manufacture of a medicament for the treatment of a medical condition treatable by said GnRH related compound is provided.

It is understood that the combinations of all embodiments described herein are also envisaged in the present invention.

The present invention will now be described in more detail with reference to the following examples. However, these examples are given for the purpose of illustration and are not to be construed as limiting the scope of the invention.

EXAMPLES

1. Application of Co-Solvent During the Preparation of Acyline (1) Preparation of Acyline Batches The six different acyline batches are described in FIG. 1, which summarizes the variations in the lyophilization procedure, which is the last step of the preparation of acyline. For lots XF 173/315-125, XF 185/165-133 and XF 173/315-151A, a co-solvent system is used in the lyophilization step. Water is used as a solvent for other batches. The batches and the associated lyophilization solvents are also illustrated in FIG. 1. The acyline may be prepared according to methods known to one of skill in the art, for example U.S. Pat. No. 6,747,125, or processes described in the present application.

Example 1

The study of gelation for different acyline batches in propylene glycol is carried out and the result is summarized in FIG. 2. The 9% and 16.7% of acyline samples are prepared by using the acyline batches listed in FIG. 1. The 9% acyline sample of XF 173/315-125, XF 185/165-133 and XF 173/315-151A are prepared by using acyline prepared via use of a co-solvent during the lyophilization step. The acyline batches of XF 173/315-125, XF 185/165-133 and XF 173/315-151A appear clear and non-viscous after 2 hours. Other batches which are lyophilized by using water as a solvent did not appear as clear and non-viscous solutions due to the presence of gelled acyline.

Example 2

The gelation of different acyline drug batches in water is investigated and the results are summarized in FIG. 3. The 0.5% and 1% acyline samples are prepared by using the acyline batches listed in FIG. 1. The 0.5% and 1% of acyline samples of XF 173/315-125, XF 185/165-133 and XF 173/315-151A which are prepared by using co-solvent during the lyophilization step appear clear and non viscous upon dissolving in water.

Example 3

The tendency of gelation of different acyline batches in standardized microemulsion (SM) is investigated. The result is summarized in FIG. 4(a). The formulation of the standard micro emulsion is shown in FIG. 4(b). The 5 mg and 10 mg formulations of acyline in a microemulsion are prepared by using the acyline lots synthesized in FIG. 1. 5 mg and 10 mg dose of acyline batches of XF 173/315-151A which are prepared by using co-solvent during the lyophilization step appeared clear and transparent after 2 hours.

2. Application of Anti-Gelling Agents in the Formulation of Acyline Compositions General Procedures of Comparison Experiments Different concentrations of acyline composition are prepared by adding acyline to pH 6.8 buffer solution either at room temperature or 37° C. All acyline solutions contain 0.6 mg/mL sodium caprate (sodium caprate is referred as $C_{10}$ in the figures). All samples are centrifuged and filtered prior to analysis. Samples are analyzed by reverse phase HPLC with UV detection.

Example 4

10 mg acyline is transferred into 200 mL volumetric flask. A pH 6.8 buffer solution is preheated to 37° C. Then, 100 mL pre-heated buffer solution and 0.6 mg/mL sodium caprate is added to the flask to prepare a 0.1 mg/mL acyline sample. In a similar manner, Tween 80 is added to prepare a 0.1 mg/mL acyline solution with 1% Tween 80. Samples are shaken in a temperature controlled water bath at 37° C. 5 mL samples are taken at 1, 5, 10, 15, 20, 30 and 120 minutes after mixing acyline with the buffer solution. Samples are filtered immediately through 0.45 µm filters and the first 3 mL is discarded. Filtered samples are analyzed, undiluted, by reverse phase HPLC with UV detection. All samples are prepared in duplicate and the concentration was obtained for the analysis from the mean of the duplicates. The result of comparison of 1% and 0% Tween 80 at 0.1 mg/mL acyline sample is graphically recorded in FIG. 5. The results show that sodium caprate alone at a concentration below the CMC is insufficient to reduce the gelation of acyline. The addition of 1% Tween 80 successfully reduces the gelation.

Example 5

Figure 6:
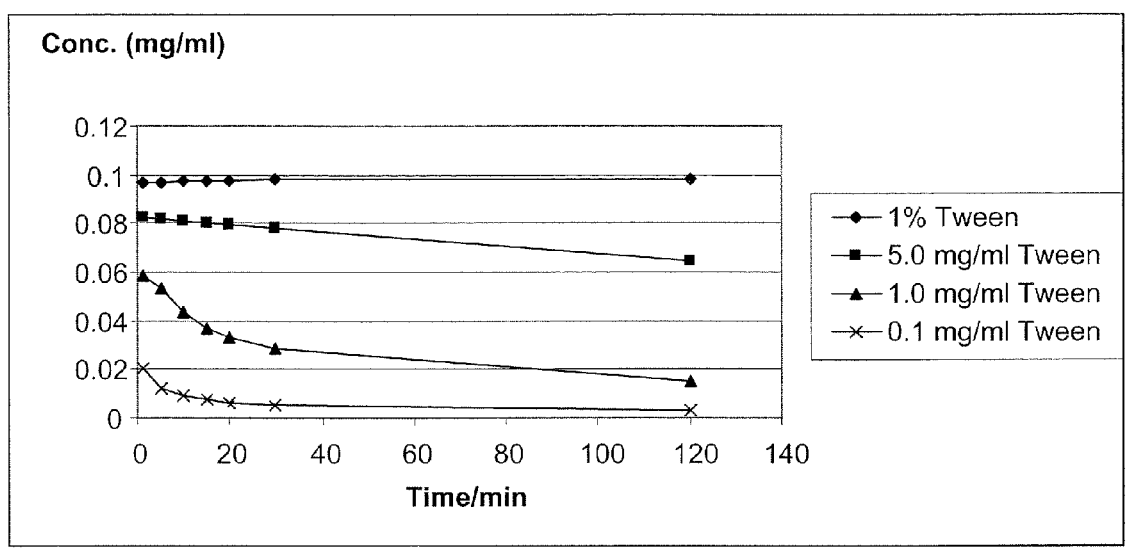
FIG. 6 graphically demonstrates the comparison results of the gelation of 0.1 mg/mL acyline sample having 5 mg/mL, 1 mg/mL, 0.1 mg/mL and 1% Tween 80.

A similar experimental procedure as Example 4 is used to prepare acyline sample for example 5. The result of comparison of 5 mg/mL, 1 mg/mL, 0.1 mg/mL and 1% Tween in phosphate buffer containing 0.6 mg/mL of sodium caprate and 0.1 mg/mL acyline is graphically recorded in FIG. 6. The results show that only 1% Tween 80 solution may completely inhibit the gelation of acyline.

Example 6

Figure 7:
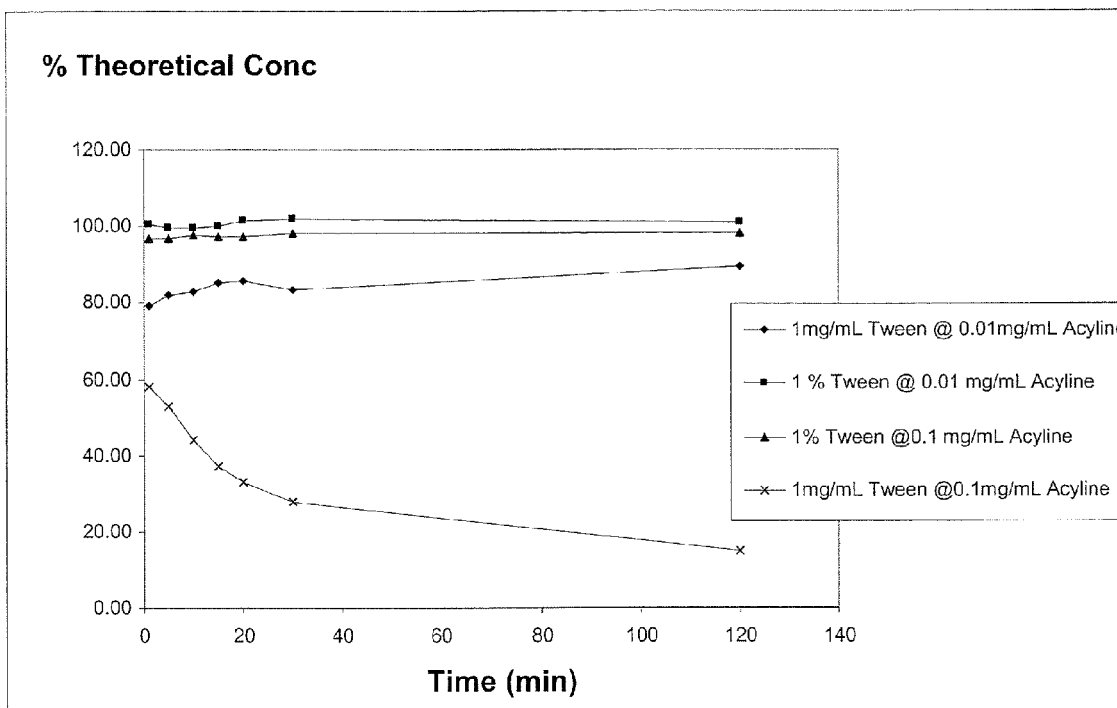
FIG. 7 graphically demonstrates the comparison results of the gelation of 0.1 and 0.01 mg/mL acyline sample having 1% and 1 mg/mL Tween 80.

A similar experimental procedure as Example 4 is used to prepare acyline sample for example 6. The result of comparison of 1% and 1 mg/mL Tween 80 in 0.1 and 0.01 mg/mL acyline sample is graphically recorded in FIG. 7. The results show that 1% Tween 80 reduces gelation for both 0.1 mg/mL and 0.01 mg/mL acyline sample.

Example 7

Figure 8:
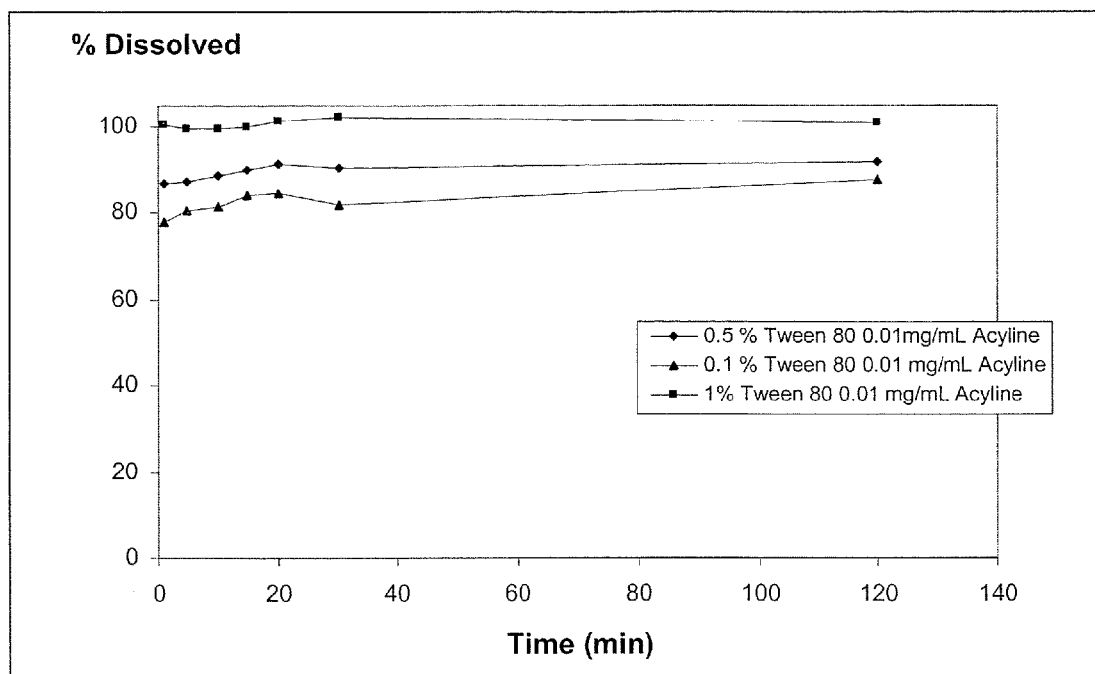
FIG. 8 graphically demonstrates the comparison results of the gelation of 0.01 mg/mL acyline sample having 0.1%, 0.5% and 1% Tween 80.

A similar experimental procedure as Example 4 is used to prepare acyline sample for example 7. The result of comparison of 0.01 mg/mL acyline samples having 0.1%, 0.5% and 1% Tween 80 is graphically recorded in FIG. 8. The results show that the acyline sample with 1% Tween 80 significantly reduces the gelation.

3. Impact of Sodium Caprate (C10) on the Tendency of Gelation of acyline in Water Example 8

Figure 9:
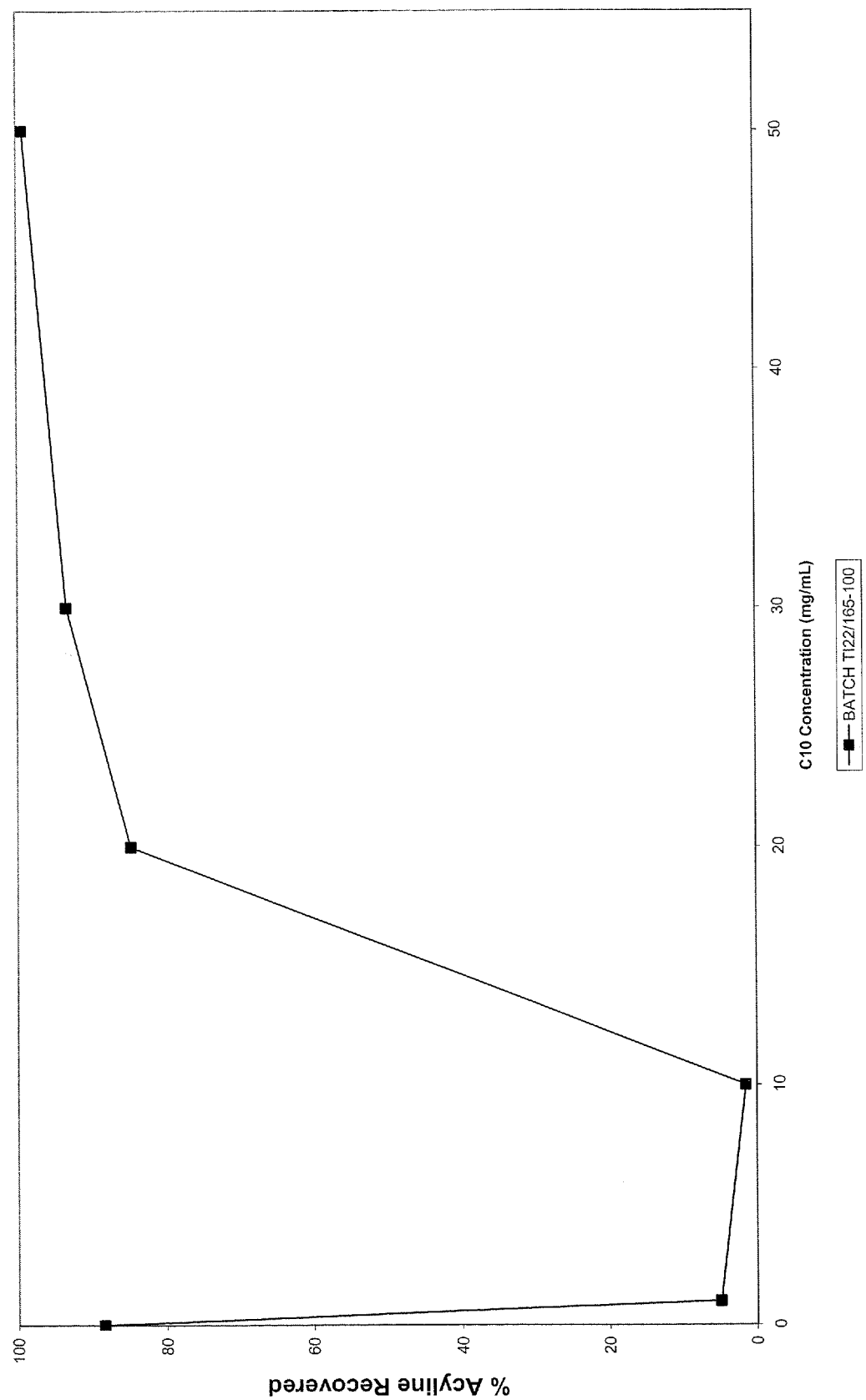
FIG. 9 graphically demonstrates the correlation between the concentration of sodium caprate and the gelation of acyline.

FIG. 9 graphically demonstrates the impact of different concentrations of sodium caprate (C10) on the tendency of gelation of acyline in water. When the concentration of sodium caprate is below 10 mg/mL, the recovery of acyline significantly decreases, which implies an increase of gelation of acyline. The investigator of the present invention believes that the increase of the gelation is due to an increased concentration of ions caused by the addition of sodium caprate. However, when the concentration of sodium caprate reaches and is above the CMC of sodium caprate (~20 mg/mL), it is observed that there is a sudden and significant increase of the recovery of acyline, which indicates an effective reduction of gelation. The CMC of sodium caprate is known as 100 mM (~20 mg/mL). (See "kinetic studies of the interaction of fatty acids with phosphatidylcholine vesicles (liposomes), Rogerson et al., *Colloids and Surfaces B*: Biointerfaces, 48, 24-34 (2006).) When the concentration of sodium caprate reaches about 50 mg/mL, the recovery of acyline is almost 100%, which indicates that the gelation is completely inhibited.

4. Application of Anti-Gelling Agents in Different Micoremulsion formulations of Acyline Samples Example 9

Figure 11:
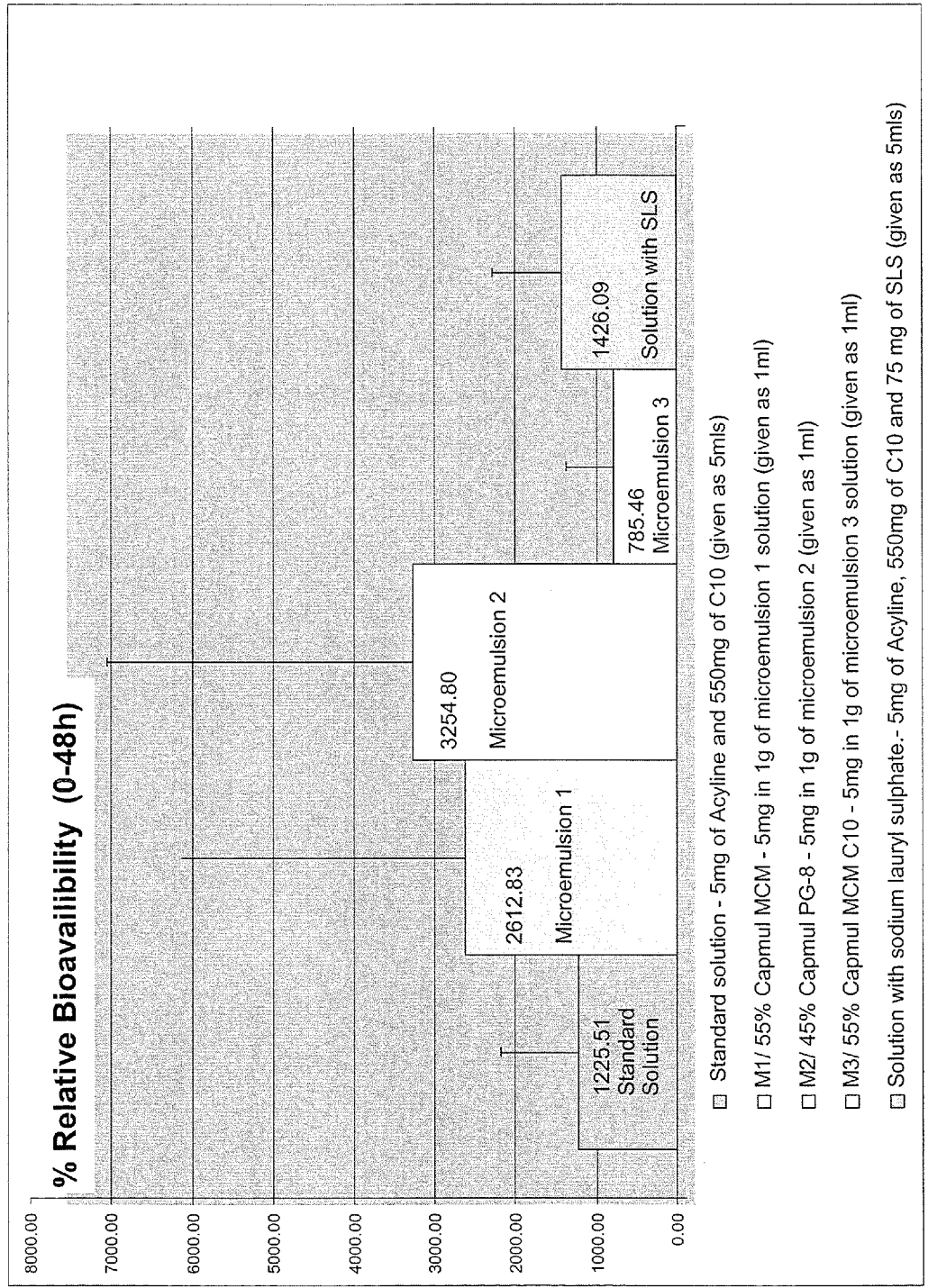
FIG. 11 graphically demonstrates the comparison results of relative bioavailability of different formulations of acyline.

FIG. 11 graphically demonstrates the relative bioavailability of various formulations of acyline in dogs. The relative bioavailability is measured by comparing the absolute bioavailability of various formulations of acyline with the absolute bioavailability of a standard formulation of acyline, which is a formulation without any anti-gelling agent. The formulation of microemulsion 1 (M1/55% Capmul MCM), microemulsion 2 (M2/45% Capmul PG-8), and microemulsion 3 (M3/55% Capmul MCM C10) are illustrated in FIG. 10(a) through (c). The formulation of the standard solution is 5 mg acyline, 550 mg sodium caprate and 5 mL purified water. "$C_{10}$" in FIGS. 10 and 11 represents sodium caprate. "SLS" in FIGS. 10 and 11 represents sodium lauryl sulphate. The comparison results in FIG. 11 show that all formulations with anti-gelling agents such as sodium caprate and sodium lauryl sulphate, increase the bioavailability of acyline from 7.8 fold to 32.5 fold.

Example 10

Figure 12:
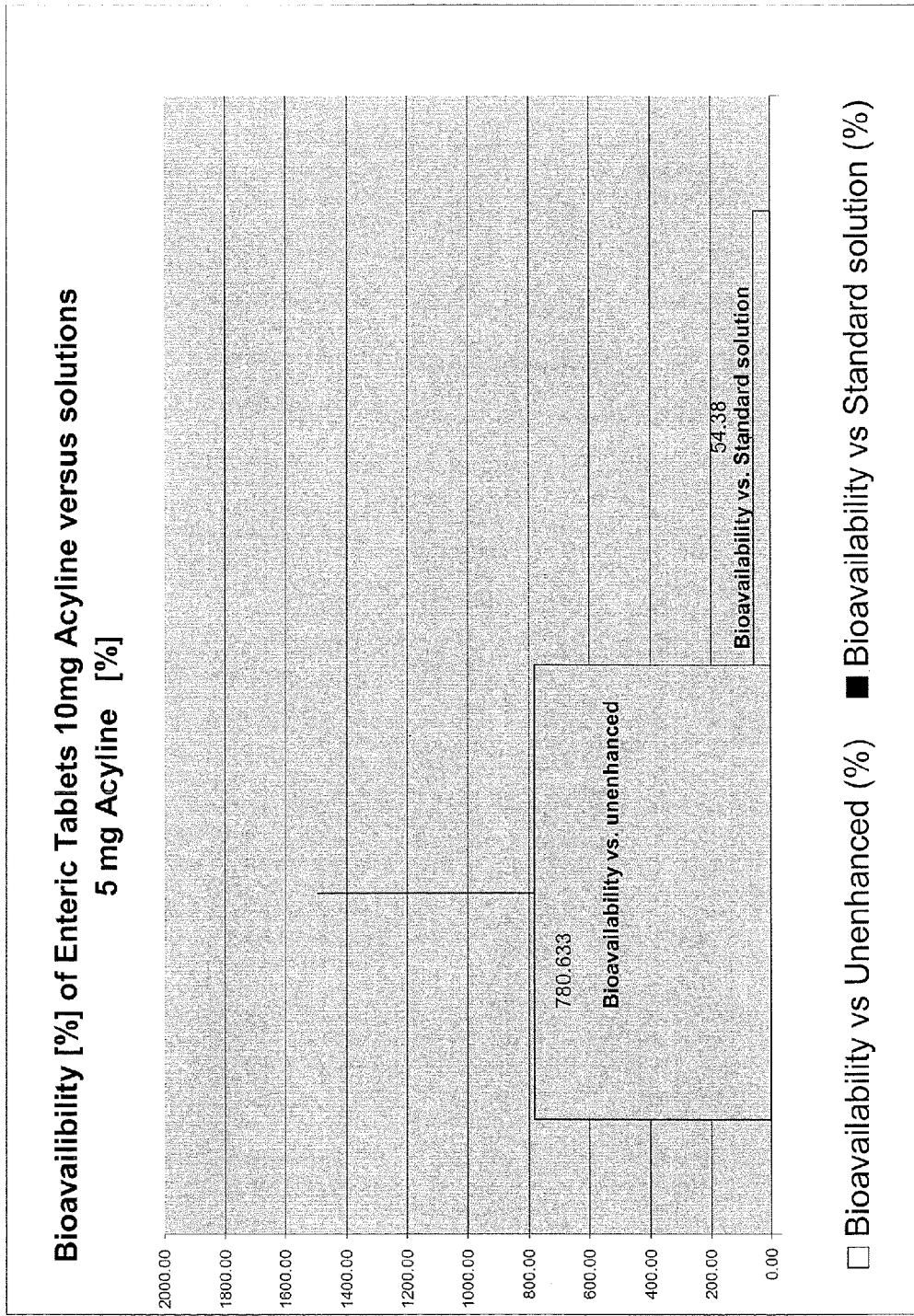
FIG. 12 graphically demonstrates the comparison results of relative bioavailability of (1) enteric tablets 10 mg acyline versus acyline sample with no surface active agent and (2) enteric tablets 10 mg acyline versus 5 mg acyline with sodium caprate sample.

FIG. 12 graphically demonstrates the relative bioavailability of (1) enteric tablets of 10 mg acyline versus unenhanced 5 mg acyline solution sample and (2) enteric tablets of 10 mg acyline versus 5 mg acyline standard sample. The formulation of acyline standard sample is 5 mg acyline, 550 mg sodium caprate and 5 mL purified water. The acyline in the tablets and the 5 mg acyline sample is prepared by using a lyophilization step with water as the solvent. The tablets contained the same amount of sodium caprate as the 5 mg acyline sample. It is observed that, the concentration of sodium caprate, 110 mg/mL, is sufficient to reduce or even inhibit gelation in the solution and enhance the bioavailability of acyline solution. FIG. 12 demonstrates that the bioavailability of enhanced tablets is significantly improved compared to unenhanced tablet.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A solid oral dosage form comprising a therapeutically effective amount of one or more GnRH antagonists selected from the group consisting of acyline, abarelix, cetrorelix, degarelix, ganirelix, and a pharmaceutically acceptable salt thereof, and a sufficient amount of at least one anti-gelling agent to reduce the gelation of the GnRH antagonist, wherein at least one anti-gelling agent is a medium chain fatty acid salt and has a carbon chain length of from about 8 to about 14 carbon atoms;
wherein the solid oral dosage form is prepared by mixing the one or more GnRH antagonists with the at least one anti-gelling agent;
wherein the final step of the preparation of the GnRH antagonist is conducted in the presence of a co-solvent system in a manner such that the gelation of the GnRH antagonist is reduced, wherein the co-solvent system comprises water and at least one water-miscible solvent selected from the group consisting of methanol, ethanol, iso-propanol, tert-butanol, acetonitrile and methylene chloride.

2. The solid oral dosage form of claim 1, wherein the gelation of at least 90% of the GnRH antagonist is inhibited.

3. The solid oral dosage form of claim 1, wherein the anti-gelling agent is selected from the group consisting of sodium caprylate, sodium caprate and sodium laurate.

4. The solid oral dosage form of claim 1, wherein the weight ratio of the water miscible solvent to water is in the range of about 1/1000 to about 99/1.

5. The solid oral dosage form of claim 1, further comprising a rate-controlling polymer.

6. The solid oral dosage form of claim 5, wherein the rate-controlling polymer is a polymer derived from acrylic or methacrylic acid and esters or copolymers derived from acrylic or methacrylic acid.

7. The solid oral dosage form of claim 5, wherein the rate-controlling polymer is hydroxypropylmethylcellulose (HPMC).

8. The solid oral dosage form of claim 1 further comprising one or more excipients selected from the group consisting of rate-controlling polymeric materials, diluents, lubricants, disintegrants, plasticizers, anti-tack agents, opacifying agents, pigments, and flavorings.

9. The solid oral dosage form of claim 1, having thereon an enteric coating.

10. The solid oral dosage form of claim 9, wherein the enteric coated solid oral dosage form is a tablet or capsule.

11. The solid oral dosage form of claim 1, wherein the solid oral dosage form is in a form selected from the group consisting of a multiparticulate form, a sustained-release form, and an instant release form.

12. The solid oral dosage form of claim 1, further comprising at least one diluent which is an inert filler selected from the group consisting of microcrystalline cellulose, lactose, dibasic calcium phosphate, and saccharides.

13. The solid oral dosage form of claim 12, wherein at least one inert filler is a saccharide selected from the group consisting of mannitol, starch, sorbitol, sucrose, and glucose.

14. The solid oral dosage form of claim 1, further comprising at least one lubricant selected from the group consisting of colloidal silicon dioxide, talc, magnesium stearate, calcium stearate, and stearic acid.

15. The solid oral dosage form of claim 1, further comprising at least one disintegrant selected from the group consisting of lightly crosslinked polyvinylpyrrolidone, corn starch, potato starch, maize starch and modified starches, croscarmellose sodium, crospovidone, and sodium starch glycolate.

16. The solid oral dosage form of claim 1, wherein the oral dosage form is a tablet or a capsule.

17. A process for preparing a GnRH antagonist selected from the group consisting of acyline, abarelix, cetrorelix, degarelix, ganirelix, and a pharmaceutically acceptable salt thereof, wherein the process comprises preparing the GnRH antagonist in the presence of a co-solvent system in a manner such that the gelation of the GnRH antagonist is reduced; and wherein the co-solvent system comprises water and at least one water-miscible solvent selected from the group consisting of methanol, ethanol, iso-propanol, tert-butanol, acetonitrile and methylene chloride.

18. The process of claim 17 wherein the weight ratio of the water miscible solvent to water is in the range of about 1:1000 to about 99:1.

19. A method for preparation of a solid oral dosage form of one or more GnRH antagonists selected from the group consisting of acyline, abarelix, cetrorelix, degarelix, ganirelix, and a pharmaceutically acceptable salt thereof, wherein the process comprises mixing the GnRH antagonists with one or more anti-gelling agents, wherein at least one anti-gelling agent is a medium chain fatty acid salt and has a carbon chain length of from about 8 to about 14 carbon atoms;

wherein the final step of the preparation of the GnRH antagonist is conducted in the presence of a co-solvent system in a manner such that the gelation of the GnRH antagonist is reduced, wherein the co-solvent system comprises water and at least one water-miscible solvent selected from the group consisting of methanol, ethanol, iso-propanol, tert-butanol, acetonitrile and methylene chloride.

20. A method of treating a medical condition treatable by a GnRH antagonist comprising administering to a patient suffering from said condition a solid oral dosage form comprising a therapeutically effective amount of one or more GnRH antagonists selected from the group consisting of acyline, abarelix, cetrorelix, degarelix, ganirelix, and a pharmaceutically acceptable salt thereof, and a sufficient amount of at least one anti-gelling agent to reduce the gelation of the GnRH antagonist, wherein at least one anti-gelling agent is a medium chain fatty acid salt and has a carbon chain length of from about 8 to about 14 carbon atoms;

wherein the solid oral dosage form is prepared by mixing the one or more GnRH antagonists with the at least one anti-gelling agent;

wherein the final step of the preparation of the GnRH antagonist is conducted in the presence of a co-solvent system in a manner such that the gelation of the GnRH antagonist is reduced, wherein the co-solvent system comprises water and at least one water-miscible solvent selected from the group consisting of methanol, ethanol, iso-propanol, tert-butanol, acetonitrile and methylene chloride.

21. The method of claim 20, wherein the gelation of at least 90% of the GnRH antagonist is inhibited.

22. The method of claim 20, wherein the medical condition is sex hormone dependent diseases selected from the group consisting of prostate hyperplasia, prostate cancer, breast cancer, endometrial cancer, ovarian cancer, endometriosis, precocious puberty, and contraception.

23. The method of claim 20, wherein the anti-gelling agent is selected from the group consisting of sodium caprylate, sodium caprate and sodium laurate.

24. The method of claim 20, wherein the weight ratio of the water miscible solvent to water is in the range of about 1/1000 to about 99/1.

25. The method of claim 20, wherein said solid oral dosage form further comprises a rate-controlling polymer.

26. The method of claim 25, wherein the rate-controlling polymer is a polymer derived from acrylic or methacrylic acid and esters or copolymers derived from acrylic or methacrylic acid.

27. The method of claim 25, wherein the rate-controlling polymer is hydroxypropylmethylcellulose (HPMC).

28. The method of claim 20, wherein the solid oral dosage form further comprises one or more excipients selected from the group consisting of rate-controlling polymeric materials, diluents, lubricants, disintegrants, plasticizers, anti-tack agents, opacifying agents, pigments, and flavorings.

29. The method of claim 20, wherein the solid oral dosage form is in the form of a tablet or capsule.

30. The method of claim 20, wherein the solid oral dosage form is in a form selected from the group consisting of a multiparticulate form, a sustained-release form, and an instant release form.

31. The method of claim 20, wherein the solid oral dosage form comprises at least one diluent which is an inert filler selected from the group consisting of microcrystalline cellulose, lactose, dibasic calcium phosphate, and saccharides.

32. The method of claim 31, wherein at least one inert filler is a saccharide selected from the group consisting of mannitol, starch, sorbitol, sucrose, and glucose.

* * * * *

UNITED STATES PATENT AND TRADEMARK OFFICE
CERTIFICATE OF CORRECTION

PATENT NO. : 8,999,383 B2  Page 1 of 1
APPLICATION NO. : 12/437012
DATED : April 7, 2015
INVENTOR(S) : Lee et al.

It is certified that error appears in the above-identified patent and that said Letters Patent is hereby corrected as shown below:

In the Specification

Column 12, Line 62: Please correct "LO 30 mole,"
to read -- EO 30 mole, --

Signed and Sealed this
Twenty-seventh Day of October, 2015

Michelle K. Lee
*Director of the United States Patent and Trademark Office*